(12) United States Patent
Bossmann et al.

(10) Patent No.: US 8,969,027 B2
(45) Date of Patent: Mar. 3, 2015

(54) PROTEASE ASSAY

(75) Inventors: Stefan H. Bossmann, Manhattan, KS (US); Deryl L. Troyer, Manhattan, KS (US); Matthew T. Basel, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 421 days.

(21) Appl. No.: 12/920,771

(22) PCT Filed: Mar. 3, 2009

(86) PCT No.: PCT/US2009/035875
§ 371 (c)(1),
(2), (4) Date: Sep. 2, 2010

(87) PCT Pub. No.: WO2009/111470
PCT Pub. Date: Sep. 11, 2009

(65) Prior Publication Data
US 2011/0014125 A1 Jan. 20, 2011

Related U.S. Application Data

(60) Provisional application No. 61/067,891, filed on Mar. 3, 2008.

(51) Int. Cl.
| | | |
|---|---|---|
| *C12Q 1/37* | (2006.01) | |
| *C12N 11/06* | (2006.01) | |
| *A61K 49/14* | (2006.01) | |
| *C12N 11/00* | (2006.01) | |
| *C12N 11/14* | (2006.01) | |
| *A61K 49/00* | (2006.01) | |
| *B82Y 15/00* | (2011.01) | |
| *C07K 5/113* | (2006.01) | |
| *C07K 7/06* | (2006.01) | |
| *C07K 7/08* | (2006.01) | |
| *G01N 33/58* | (2006.01) | |
| *C12N 11/02* | (2006.01) | |
| *C12N 11/04* | (2006.01) | |

(52) U.S. Cl.
CPC ......... *A61K 49/0065* (2013.01); *A61K 49/0036* (2013.01); *A61K 49/0056* (2013.01); *A61K 49/0067* (2013.01); *A61K 49/0093* (2013.01); *B82Y 15/00* (2013.01); *C07K 5/1021* (2013.01); *C07K 7/06* (2013.01); *C07K 7/08* (2013.01); *C12Q 1/37* (2013.01); *G01N 33/588* (2013.01); *Y10S 977/773* (2013.01); *Y10S 977/774* (2013.01)
USPC .............. 435/24; 424/9.1; 435/174; 435/176; 435/177; 977/773; 977/774

(58) Field of Classification Search
USPC ...................... 424/9.1; 435/24, 174, 176, 177; 977/773, 774
See application file for complete search history.

(56) References Cited

U.S. PATENT DOCUMENTS 7,067,320 B2 * 6/2006 Klimant .......................... 436/74
2006/0286379 A1 12/2006 Gao

FOREIGN PATENT DOCUMENTS

| EP | 1 052 293 | 11/2000 |
| WO | 2007/027640 | 3/2007 |
| WO | 2007/107156 | 9/2007 |

OTHER PUBLICATIONS

Cai et al., 2007. Nanoplatforms for Targeted Molecular Imaging in Living Subjects. Small, vol. 3, Issue 11, pp. 1840-1854.*
Pham et al. 2004. Developing a Peptide-Based Near-Infrared Molecular Probe for Protease Sensing. Bioconjugate Chem., vol. 15, pp. 1403-1407.*
Sounderya et al. 2008. Use of Core/Shell Structured Nanoparticles for Biomedical Applications. Recent Patents on Biomedical Engineering 2008, vol. 1, No. 1 Jan. 2008, pp. 34-42.*
Rochford et al. 2007.Tetrachelate Porphyrin Chromophores for Metal Oxide Semiconductor Sensitization: Effect of the Spacer Length and Anchoring Group Position. J. Am. Chem. Soc., vol. 129, No. 15, pp. 4655-4665.*
Li et al. 2003. Large-Scale Synthesis of Nearly Monodisperse CdSe/CdS Core/Shell Nanocrystals Using Air-Stable Reagents via Successive Ion Layer Adsorption and Reaction. J. Am. Chem. Soc., vol. 125, No. 41, pp. 12567-12575.*
Law et al. 2008. Structural Modification of Protease Inducible Preprogrammed Nanofiber Precursor. Biomacromolecules, vol. 9, No. 2, pp. 421-425.*
Chau et al. 2008. Incorporation of a matrix metalloproteinase-sensitive substrate into self-assembling peptide—A model for biofunctional scaffolds. Biomaterials, vol. 29, pp. 1713-1719.*
Dictionary meaning Chromophore Luminophore Viologen. 2012.*
Lahav et al (2000). Photoelectrochemistry with Integrated Photosensitizer-Electron Acceptor and Au-Nanoparticle Arrays. J. Am. Chem. Soc., vol. 122, pp. 11480-11487.*
Garcia et al., "Biological and Clinical Significance of Cathepsin D in Breast Cancer Metastasis," Stem Cells, 1996, vol. 14, 642-650.
Hall et al., "Enhanced Invasion of Hormone Refractory Prostate Cancer Cell Through Hepatocyle Growth Factor (HGF) Induction of Urokinase-Type Plasminogen Activator (u-PA)," The Prostate, 2004, vol. 59, 167-176.
Prasad et al, "Digestive Ripening of Thiolated Gold Nanopaiticles: The Effect of Alkyl Chain Length," Langmuir, 2002, vol. 18, No. 20, 7515-7520.
Wang et al., "Synthesis of Functionalized Bimagnetic Core/Shell Fe/Fe3O4 Nanoparticles for the Treatment of Cancer," Copyright American Chemical Society, Abstract from 44th Midwest Regional Meeting of the American Chemical Society, Iowa City, Iowa, United States, Oct. 21-24, 2009.

(Continued)

*Primary Examiner* — Jon P Weber
*Assistant Examiner* — Kailash C Srivastava
(74) *Attorney, Agent, or Firm* — Hovey Williams LLP

(57) ABSTRACT

The present invention provides a diagnostic reagent or assay for assessing the activity of a protease in vivo or in vitro and methods of detecting the presence of a cancerous or precancerous cell. The assays are comprised of two particles linked via an oligopeptide linkage that comprises a consensus sequence specific for the target protease. Cleavage of the sequence by the target protease can be detected visually or using various sensors, and the diagnostic results can be correlated with cancer prognosis.

16 Claims, 10 Drawing Sheets

(56) References Cited

OTHER PUBLICATIONS

Wang et al., "Synthesis of 'Light Switches for Urokinase Activity' Using Consensus (Cleavage) Sequences Between Bimagnetic Core/Shell Fe/Fe3O4 Nanoparticles and a Porphyrin," Copyright American Chemical Society, Abstract from 44th Midwest Regional Meeting of the American Chemical Society, Iowa City, Iowa, United States, Oct. 21-24, 2009.
Samarakoon et al., "Early Detection of Cancer through Matrix Metalloproteinases," Copyright American Chemical Society, Abstract from 44th Midwest Regional Meeting of the American Chemical Society, Iowa City, Iowa, United States, Oct. 21-24, 2009.
Samarakoon et al., "Test of an in-Vivo Sensor for Urokinase Using Fluorescence Microscopy," Copyright American Chemical Society, Abstract from 44th Midwest Regional Meeting of the American Chemical Society, Iowa City, Iowa, United States, Oct. 21-24, 2009.
Kalita et al, "Optical and Electronic Properties of Metal and Semiconductor Nanostructures," Nanoscale Materials in Chemistry, Second Edition, Edited by Klabunde and Richards, 2009, John Wiley & Sons, Inc., Chapter 16, 535-572.
Duhamel, "Pyrene fluorescence to study polymeric systems," Molecular Interfacial Phenomena of Polymers and Biopolymers, 2005, vol. 7, 214-221.
Periasamy and Day, Eds., "Book Review: Molecular Imaging, FRET Microscopy and Spectroscopy," Journal of Biomedical Optics, 2006, vol. 11, No. 6, 069901-1-069901-2.
Lopez Arbeloa et al., "Photophysics of amino-aromatic laser dyes," Trends in Photochemistry & Photobiology, 1994, vol. 3, No. 1, pp. 145-155.
Charrois et al., "Drug release rate influences the pharmokinetics, biodistribution, therapeutic activity, and toxicity of peglated liposomal doxorubicin formations in murine breast cancer," Biochimica et Biophysica Acta 1663, 2004, 167-177.
Ito et al., "Tumor regression by combined immunotherapy and hyperthermia using magnetic nanoparticles in an experimental subcutaneous murine melanoma," Cancer Sci, 2003, vol. 94, No. 3, 308-313.
Bremer et al., "Optical imaging of Spontaneous Breast Tumors Using Protease Sensing 'Smart' Optical Probes," Investigative Radiology, 2005, vol. 40, No. 6, 321-327.
International Search Report and Written Opinion dated Oct. 21, 2009, in corresponding PCT application PCT/US2009/035875 filed on Mar. 3, 2009.
Kumaraswamy et al., "Fluoresent-conjugated polymer superquenching facilitates highly sensitive detection of proteases," The National Academy of Sciences of the USA, 2004, vol. 101, No. 20, 7511-7515.
International Preliminary Report on Patentability dated Sep. 16 2010, in corresponding PCT application PCT/US2009/035875 filed on Mar. 3, 2009.
Foekens et al., "The Urokinase System of Plasminogen Activation and Prognosis in 2780 Breast Cancer Patients," Cancer Res., 60, 2000, 636-643 (http://cancerres.aacrjournals.org/content/60/3/636.full).
Duffy et al., "Urokinase-Plasminogen Activator, a New and Independent Prognostic Marker in Breast Cancer" Cancer Res, 1990, 50, 6827-6829.
Andreasen et al., "The Urokinase-Type Plasminogen Activator System in Cancer Metastasis: A Review," Int. J. Cancer, 1997, 72, 1-22
Turk et al., "Determination of protease cleavage site motifs using mixture-based oriented peptide libraries," Nature Biotechnology, 2001, vol. 19, 661-667.
Yasuda et al., "A new selective substrate for cathespin E based on the cleavage site sequence of a2-macroglubulin," Biological Chemistry, 2005, 386, 299-305.
Warnecke et al., "Synthesis, Cleavage Profile, and Antitumor Efficacy of an Albumin-Binding Prodrug of Methotrexate that is Cleaved by Plasmin and Cathepsin B," Arch. Pharm. Chem. Life Sci., 2007, 340, 389-395.
Yasuda et al, "Characterization of New Fluorogenic Substrates for the Rapid and Sensitive Assay of Cathepsin E and Cathepsin D," Journal of Biochemistry, 1999, vol. 125, No. 6, 1137-1143.

Link et al., "Spectral Properties and Relaxation Dynamics of Surface Plasmon Electronic Osciliations in Gold and Silver Nanodots and Nanorods," J. Phys Chem. B, 1999, vol. 103, No. 40, 8410-8426.
Weinmann, "History of the Development and Applications of Coumarin and Coumarin-related Compounds," Coumarins: Biology, Applications and Mode of Action, 1997, John Wiley & Sons Ltd., Chapter 1, 1-22.
Kostova, "Synthetic and Natural Coumarins as Antioxidants," Mini-Reviews in Medicinal Chemistry 2006, vol. 6, No. 4, 365-374.
Abernethy, "The Historical and Current Interest in Courmarin," Journal of Chemical Education 1969, vol. 46 No. 9, 561-568.
http://www.coumarins.com, printed main screen from website on Dec. 6, 2010, 1 page.
Fagadar-Cosma et al., "Combinatorial Synthesis and Characterization of New Asymmetric Porphyrins as Potential Photosensitizers in Photodynamic Therapy," Combinatorial Chemistry & High Throughput Screening, 2007, vol. 10, No. 6, 466-472.
Patterson, "Fluorescent Proteins for Cell Biology," Methods in Molecular Biology, 2007, Chapter 5, 411: Reporter Genes: A Practical Guide, 47-80.
Fallahpour, "The Higher Oligopyridines and their Metal Complexes," Current Organic Synthesis, 2006, vol. 3, No. 1, 19-39.
Paul, "Ruthenium, osmium and rhodium complexes of polypyridyl ligands: Metal-promoted activities, stereochemical aspects and electrochemical properties," Proceedings Indian Academy of Sciences, Chemical Sciences, 2002, vol. 114, No. 4, 269-276.
Ponce et al., "Hyperthermia mediated liposomal drug delivery," International Journal of Hyperthermia, 2006, vol. 22, No. 3, 205-213.
Torchilin, "Multifunctional nanocarriers," Advanced Drug Delively Reviews 2006, 58, 1532-1555.
Chang et al., "Protease-Activated Quantum Dot Probes" Biophotonics and New Therapy Frontiers, Proc. of SPIE, vol. 6101, 2006, 61911E-1-61911E-10.
Tiefenauer, "Magnetic Nanoparticies as Contrast Agents for Medical Diagnosis," Nanotechnology in Biology and Medicine, 2007, Chapter 29, 1-20.
Laurent et al., "Magnetic Iron Oxide Nanoparticles: Synthesis, Stabilization, Vectorization, Physiochemical Characterizations, and Biological Applications," Chem. Rev., 2008, vol. 108, No. 6, 2064-2110.
Biju et al., "Semiconductor quantum dots and metal nanoparticles: syntheses, optical properties, and biological applications," Analytical and Bioanalytical Chemistry, 2008, 391, 2469-2495.
Kjaergaard et al., "Structure and ligand interactions of the urokinase receptor (uPAR)," Frontiers in Bioscience, 2008, 13, 5441-5461.
Elliott et al., "Gold nanostell thermal confinement of conformal laser thermal therapy in liver metastasis," Proceedings of SPIE, 2008, 6865 (Nanoscale Imaging, Sensing, and Actuation for Biomedical Applications V), 68650Q/1-68650Q/8.
Choi et al., "Renal clearance of quantum dots," Nature Biotechnology, 2007, vol. 25, No. 10, 1165-1170.
Hutter et al., "Exploitation of Localized Surface Plasmon Resonance," Advanced Materials, 2004, vol. 16, No. 19, 1686-1706.
Vail et al., "Pegylated Liposomal Doxorubicin: Proof of Principle Using Preclinical Animal Models and Pharmacokinetic Studies," Seminars in Oncology, 2004, 31, 16-35.
Charrois et al., "Rate of biodistribution of STEALTH liposomes to tumor and skin: influence of liposome diameter and implications for toxicity and therapeutic activity," Biochem. Biophys. Acta, 1609, 2003, 102-108.
Shinkai et al., "Functional Magnetic Particles for Medical Application," J. Biosci. Bioeng., 2002, vol. 94, No. 6, 606-813.
Simoes et al., "On the formulation of pH-sensitive, liposomes with long circulation times," Adv. Drug. Deliv. Rev., 56, 2004, 947-965.
Mulet et al., "Nanoscale radiative heat transfer between a small particle and a plane surface," Applied Physics Letters, 2001, vol. 78, No. 19, 2931-2933.
Plech et al., "Laser-induced heating and melting of gold nanoparticles studied by time-resolved x-ray scattering" Physical Review B, 2004, 70, 195423-1-195423-7.

(56) References Cited

OTHER PUBLICATIONS

Dabbousi et al, "(CdSe)ZnS Core—Shell Quantum Dots: Synthesis and Characterization of a Size Series of Highly Luminescent Nanocrystallites," J. Phys. Chem. B. 1997, vol. 101, No. 46, 9463-9475.

Fisher et al., "Emission Intensity Dependence and Single-Expotential Behavior in Single Colloidal Quantum Dot Fluorescence Lifetimes," J. Phys. Chem. B, 2004, vol. 108, No. 1, 143-148.

Lakowicz, "Radiative Decay Engineering: Biophysical and Biomedical Applications," Analytical Biochemistry, 2001, 298, 1-24.

Steinfeld, "Quenching of Fluorescence in Small Molecules," Accounts of Chemical Research, 1970, vol. 3, 313-320.

Kondon et al., "Origin of Size-Dependent Energy Transfer from Photoexcited CdSe Quantum Dots to Gold Noparticles," J. Phys. Chem. C, 2008; vol. 112, No. 17, 6695-6699.

Kulakovich et al., "Enhanced Luminescence of CdSe Quantum Dots on Gold Colloids," Nano Lett., 2002, vol. 2, No. 12, 1449-1452.

Duffy, "Proteases as Prognostic Markers in Cancer," Clinical Cancer Research, 1996, vol. 2, 613-618.

Johansson et al., "Matrix metalloproteinases in tumor invasion," Cellular and Molecular Life Sciences, 2000, 57, 5-15.

Khasigov et al., "Role of Matrix Metalloproteinases and Their Inhibitors in Tumor Invasion and Metastasis," Biochemistry (Moscow, Russian Federation), 2003, vol. 68. No. 7, 711-717.

Duffy, "Urokinase-type plasminogen activator: a potent marker of metastatic potential in human cancers," Biochemical Society Transactions, 2002, vol. 30, Part 2, 207-210.

Liu et al., "Targeting of Tumor Cells by Cell Surface Urokinase Plasminogen Activator-dependent Anthrax Toxin," Journal of Biological Chemistry, 2001, vol. 276, No, 21, 17976-17984.

Winnik et al., "Cononsolvency of Ppoly(N-isopropylacrylamide) in Mixed Water-Methanol Solutions: A Look at Spin-Labeled Polymers," Macromolecules, 1992, vol. 25, No. 22, 6007-6017.

Winnik et al., "Cononsolvency of Poly(N-isopropylacrylamide): A Look at Spin-Labeled Polymers in Mixtures of Water and Tetrahydrofuran," Macromolecules, 1993, vol. 26, No. 17, 4577-4585.

Schild et al., "Cononsolvency in Mixed Aqueous Solutions of Poly(N-isopropylacrylamide)," Macromolecules, 1991, vol. 24, No. 4, 948-952.

Ottaviani et al., "Phase Separation of Poly(N-isopropylacrylamide) in Mixtures of Water and Methanol: A Spectroscopic Study of the Phase-Transition Process with a Polymer Tagged with a Fluorescent Dye and a Spin Label," Helv. Chim. Acta, 2001, vol. 84, 2476-2492.

Leatherdale et al., "On the Absorption Cross Section of CdSe Nanocrystal Quantum Dots," Journal of Physical Chemistry B, 2002, vol. 106, No. 31, 7619-7622.

Meijer et al., "Effect of restraint and injection methods on heart rate and body temperature in mice," Laboratory Animals, 2006, 40, 382-391.

Liao et al., "Biomedical applicatons of plasmon resonant metal nanoparticles," Nanomedicine, 2006, 1, 201-208.

Roux et al., "Polymer based pH-sensitve carriers as a means to improve the cytoplasmic delivery of drugs," International Journal of Pharmaceutics, 2002, 242, 25-36.

Park et al., "Fabrication of Magnetic Core@Shell Fe Oxide@Au Nanoparticles for Interfacial Bioactivity and Bio-separation," Langmuir, 2007, vol. 23, No. 17, 9050-9056.

Wang et al., "Monodispersed Core—Shell Fe3O4@Au Nanoparticles," J. Phys. Chem. B, 2005, vol. 109, No. 46. 21593-21601.

Sun et al., "Theoretical Study on Gold-Coated Iron Oxide Nanostructure: Magnetism and Bioselectivity for Amino Acids," J. Phys. Chem. C, 2007, vol. 111, No. 11, 4159-4163.

Pons et al., "On the Quenching of Semiconductor Quantum Dot Photoluminescence by Proximal Gold Nanoparticles," Nano Letters, 2007, vol. 7, No. 10, 3157-3164.

Dahal et al., "Synthesis of Water-Soluble Iron-Gold Alloy Nanoparticles," Chemistry of Materials, 2008 vol. 20, No. 20, 6389-6395.

Leaym et al.. "Synthesis of Water-Soluble Highly Charged and Methylene-Bridged Resorcin[4]arenes," Synthesis, 2008, No. 6, 932-942.

Hu et al., "Heat Dissipation of Au Particles in Aqueous Solution: Relaxation Time versus, Size," J. Phys. Chem. B, 2002, vol. 106, No. 28, 7029-7033.

Oldenburg et al., "Infrared extinction properties of gold nanoshells," Applied Physics Letters, 1999, vol. 75, No. 19, 2897-2899.

Koole at el., "Time Dependent Photoluminescence Spretroscopy as a Tool to Measure the Ligand Exchange Kinetics on a Quantum Dot Surface," ACS Nano, 2008, vol. 2, No. 8, 1703-1714.

Jain et al., "On the Universal Scaling Behavior of the Distance Decay of Plasmon Coupling in Metal Nartoparticle Pairs: A Plasmon Ruler Equation," Nano Lett, vol. 7, No. 7, 2007, 2080-2088.

Juris et al., "Ru(II) Polypyridine Complexes: Photophysics, Photochemistry, Electrochemistry, and Chemiluminescence," Coordination Chemistry Reviews, 84, 1988, 85-277 Note: Reference scanned into three separate sections due to size.

Han et al, "Hyperthermia-Induced Antitumor Activity of Thermosensitive Polymer Modified Temperature-Sensitive Liposomes," Journal of Pharmaceutical Sciences, vol. 95, No. 9, 2006, 1909-1917.

Boens et al., "Fluorescence Lifetime Standards for Time and Frequency Domain Fluorescence Spectroscopy," Anal. Chem., vol. 79, No. 5, 2007, 2137-2149.

Jones et al., "Solvent Effects on Emission Yield and Lifetime for Coumarin Laser Dyes. Requirements for a Rotatory Decay Mechanism," J. Phys. Chem., vol. 89, No. 2, 1985, 294-300.

Green, "The Organometallic Synthesis of Bifunctional Core/Shell Nanoparticles," Small. vol. 1, No. 7, 2005, 684-686.

Tyson et al., "Long-Range Resonance Energy Transfer to [Ru(bpy)3]2+," J. Phys, Chem., vol. 104, No. 13, 2000, 2919-2924.

Rogach, "Binary Superlattices of Nanoparticles: Self-Assembly Leads to 'Metamateriais'," Angew. Chem. Int., 43, 2004, 148-149.

Nad et al, "Photophysical Properties of Coumarin-152 and Coumarin-481 Dyes: Unusual Behavior in Nonpolar and in Higher Polarity Solvents," J. Phys. Chem., vol. 107, No. 24, 2003, 4808-4816.

Stoeva et al., "Gram-Scale Sytherisis of Monodisperse Gold Colloids by the Solvated Metal Atom Dispersion Method and Digestive Ripening and Their Organization into Two- and Three-Dimensional Structures," J. Am. Chem. Soc., vol. 124, No. 10, 2002, 2305-2311.

Hossain et al., "Novel Peptides Bearing Pyrene and Coumarin Units with or without B-Cyclodextrin in Their Side Chains Exhibit Intramolecular Fluorescence Resonance Energy Transfer," J. Am Chem. Soc., vol. 125, No. 37, 2003, 11178-11179.

Dahl et al.,"Toward Greener Nanosynthesis," Chem. Rev., vol. 107, No. 6, 2007, 2228-2269.

Eastoe et al., "Recent advances in nanoparticle synthesis with reversed micelles," Advances in Colloid and Interface Science, 128-130, 2006, 5-15.

Maye et al., "Synthesis, Processing, Assembly and Activation of Core-Shell Structured Gold Nanoparticle Catalysts," Gold Bulletin, 36/3, 2003, 75-82.

Lohse et al., "Monitoring receptor signaling by intramolecular FRET," Current Opinion Pharmacology, 7, 2007, 547-553.

Sen et al., "Surface energy transfer from rhodamine 6G to gold nanoparticles: A spectroscopic ruler," Appl. Phys. Lett., 91, 2007, 043104-1-043104-3.

Moghimi, "2: Passive Targeting of Solid Tumors: Pathophysiological Principles and Physiochemical Aspecs of Delivery Systems," Nanotechnology for Cancer Therapy, 11-18, PUb CRC Press, Ed. Amiji M., (2006).

MacDiarmid, "Synthetic Metals": A Novel Role for Organic Polymers (Nobel Lecture), Chemistry in New Zealand Sep. 2001, 8-17, Copyright The Nobel Foundation, 2001 (originally published in Angew. Chem. Int. Ed., 2001, 40, 2581).

Dani et al., "MspA Ponn—Gold Nanoparticle Assemblies: Enhanced Binding through a Controlled Cysteine Mutation," Nano Lett., 2007, vol. xx, No. x.

Odom et al., "How Gold Nanoparticles Have Stayed in the Light: The 3M's Principle" ACS NANO, 20 18, vol. No. 4, 612-616.

(56) References Cited

OTHER PUBLICATIONS

Willets et al., "Localized Surface Plasmon Resonance Spectroscopy and Sensing," Annu Rev Phys. Chem., 2007, vol. 58, 267-297.
Wiltschi et al., "Binding assays with artificial tethered membranes using surface plasmon resonance." Methods 39, 2006, 134-146.
Wang et al., "The Emerging Use of Quantum Dots in Analysis," Analytical Letters, 2007, 40, 1497-1520.
Boatman et al., "A Safer, Easier, Faster Synthesis for CdSe Quantum Dot Nanocrystals," Journal of Chemical Education, 2005, vol. 82, No. 11, 1697-1699.
Winkler et al., "Quantum Dots: An Experiment for Physical or Materials Chemistry," Journal of Chemical Education, 2005, vol. 82, No. 11, 1700-1702.
Hu et al., "Gold nanostructures: engineering their plasmonic properties for biomedical applications," Chem. Soc. Rev., 2006, 35, 1084-1094.
Mie, Annalen Der Physik Vierte Folge, Band 25, 1908, 377-445.
Kelly et al., "The Optical Properties of Metal Nanoparticles: The Influence of Size, Shape, and Dielectric Environment," J. Phys. Chem. B, 2003, vol. 107, No. 3, 668-677.
Lee et al., "Gold and Silver Nanoparticles in Sensing and Imaging: Sensitivity of Plasmon Response to Size, Shape, and Metal Composition," J. Phys. Chem. B, 2006, vol. 110, No. 39, 19220-19225.
Protasenko et al., "Demonstration of a Low-Cost, Single Molecule Capable, Multimode Optical Microscope," Chem. Educator, 2005, vol. 10, No. 4. 269-282.
Huang et al., "Gold nartoparticies: interesting optical properties and recent applications in cancer diagnostics and therapy," Nanomedicine, 2007, 681-693.
Fukami et al., "Study for usefulness of Indocyanine green as an infrared marker," Biomarkers and Biological Spectral Imaging, Proceedings of SPIE, 2001, vol. 4259, 157-162.
Murov et al., "Handbook of Photochemistry: Second Edition Revised and Expanded,"Marcel Dekker, Inc., New York, Basel, Hong Kong, 1993, p. 27.
Lee et al., "Biological Imaging of HEK293 Cells Expressing PLCy1 Using Surface-Enhanced Raman Microscopy" Anal. Chem., 2007, vol. 79, No, 3, 916-922.
Farrer et al., "Highly Efficient Multiphoton-Absorption-Induced Luminescence from Gold Nanoparticles," Nano Letters, 2005, vol. 5, No. 6, 1139-1142.
Zhang et al., "Surfactant-Mediated Self-Assembly of Au Nanoparticle and Their Related Conversion to Complex Mesoporous Structures," Langmuir, 2008, vol. 24, No. 8, 3740-3746.
Link et al., "Alloy Formatioi of Gold—Silver Nanoparticles and the Dependence of the Plasmon Absorption in Their Composition," J. Phys. Chem. B, 1999, vol. 103, No. 18, 3529-3533.
Russier-Antoine et al., "Wavelength dependence of the hyper Rayleigh scattering response from gold nanoparticles," Journal of Chemical Physics, 2004, vol. 120, No. 22, 10748-10752.
Hamelin et al., "The Static Dielectric Constant of Liquid Water Between 274 and 418 K Near the Saturated Vapor Pressure," International Journal of Thermophysics, 1998, vol. 19, No. 5, 1359-1380.
Pinchuk et al., "Optical properties of metallic nanoparticles: influence of interface effects and interband transitions," Surface Science 557, 2004, 269-280.
Gans, Annalen der Physik, IV Folge, 1912, 881-900.
Bossmann, "6. Nanoparticles for hyperthermia treatment of cancer," Fabrication and Bio-Application of Functionalized Nanomaterials, 2009, 171-206.
Mulvaney, "Surface Plasmon Spectroscopy of Nanosized Metal Particles," Langmuir, 1996, vol. 12, No. 3, 788-800.
Jain et al., "Calculated Absorption and Scattering Properties of Gold Nanoparticles of Different Size, Shape, and Composition: Applications in Biological Imaging and Biomedicine," J. Phys. Chem. B, 2006, vol. 110, No. 14, 7238-7248.
Mohamed et al , "The 'lightening' gold nanorods: fluorescence enhancement over a million compared to the gold metal," Chemical Physics Letters 317, 2000, 517-523.
Eustis et al., "Aspect Ratio Dependence of the Enhanced Fluorescence Intensity of Gold Nanorods: Experimental and Simulation Study," J. Phys. Chem. B., 2005, vol. 109, No. 34, 16350-16356.
Jares-Erijman et al., "Imaging molecular interactions in living cells by FRET microscopy," Current Opinion in Chemical Biology, 2006, vol. 10, 409-416.
Yun et al., "Nanometal Surface Energy Transfer in Optical Rulers, Breaking the FRET Barrier," J. Am. Chem. Soc., 2005, vol. 127, No. 9, 3115-3119.
Gunnarsson et al., "Confined Plasmons in Nanofabricated Single Silver Particle Pairs: Experimental Observations of Strong Interparticle Interactions," J. Phys. Chem. B., 2005, vol. 109, No. 3, 1079-1087.
Crozier et al., "Experimental measurement of the dispersion relations of the surface plasmon modes of metal nanoparticle chains," Optics Express, 2007, vol. 15, No. 26, 17482-17493.
Reinhard et al., "Calibration of Dynamic Molecular Rulers Based on Plasmon Coupling between Gold Nanoparticles," Nano Letters, 2005, vol. 5, No. 11, 2246-2252.
Liu et al., "A nanoplasmonic molecular ruler for measuring nuclease activity and DNA footprinting," Nature Nanotechnology, 2006, vol. 1, 47-52.
Reinhard et al., "Use of plasmon coupling to reveal the dynamics of DNA bending and cleavage by single EcoRV restriction enzymes," PNAS, 2007, vol. 104, No. 8, 2667-2672.
Jain et al., "Universal Scaling of Plasmon Coupling in Metal Nanostructures: Extension from Particle Pairs to Nanoshells," Nano Letters, 2007, vol. 7, No. 9, 2854-2858.
Jain et al., "Surface Plasmon Coupling and Its Universal Size Scaling in Metal Nanostructures of Complex Geometry: Elongated Particle Pairs and Nanosphere Trimers," J. Phys. Chem. C., 2008, vol. 112, No. 13, 4954-4960.
Chan et al., "Luminescent quantum dots for multiplexed biological detection and imaging," Current Opinion in Biotechnology, 2002, vol. 13, 40-46.
Murray et al., "Synthesis and Characterization of Nearly Monodisperse CdE (E=S, Se, Te) Semiconductor Nanocrystallites," J. Am. Chem. Soc., 1993, vol. 115, No. 19, 8706-8715.
Kim et al., "Type-II Quantum Dots: CdTe/CdSe(Core/Shell) and CdSe/ZnTe(Core/Shell) Heterostructures," J. Am. Chem. Soc., 2003, vol. 125, No. 38, 11466-11467.
Bailey et al., "Alloyed Semiconductor Quantum Dots: Tuning the Optical Properties without Changing the Particle Size," J. Am. Chem. Soc., 2003, vol. 125, No. 23, 7100-7106.
Schmid et al., "Nanoparticulated Gold: Syntheses, Structures, Electronics, and Reactivities," Eur. J. Inorg. Chem., 2003, 3081-3098.
Worner et al., "Characterization of Nanostructured Surfaces Generated by Reconstitution of the Porin MspA from *Mycobacterium smegmatis*," Small, 2007, vol. 3, No. 6, 1084-1097.
Chen et al., "Quantized Capacitance Charging of Monolayer-Protected Au Clusters," J. Phys. Chem. B, 1998, vol. 102, No. 49, 9898-9907.
Chen et al., "Gold Nanoelectrodes of Varied Size: Transition to Molecule-Like Charging," Science, 1998, vol. 280, 2098-2101.
Hergert and Wriedt, Eds., "Mie Theory 1908-2008: Present developments and interdisciplinary aspects of light scatterng," Universitat Bremen, Bremen 2008. pp. 1-112.
Geier et al , "Boundary effects of molecular diffusion in nanoporous materials: A pulsed field gradient nuclear magnetic resonance study," Journal of Chemical Physics, 2004. vol. 120, No. 1, 367-373.
Hao et al., "Electromagnetic fields around silver nanoparticles and dimers," Journal of Chemcal Physics, 2004, vol. 120, No. 1, pp. 357-366.
Chen et al., "A new temperature- and pH-responsive copolymer for possible use in protein conjugation," Macromol. Chem. Phys., 1995, 196, 1251-1259.
Zhong et al., "Synthesis and Assembly of Alloy and Core-Shell Nanoparticles for Sensor Applications," Polymer Preprints, 2006, 47(2), 941-942.
Xia et al., "Muliplex Detection of Protease Activity with Quantum Dot Nanosensors Prepared by Intein-Mediated Specific Bioconjugation," Analytical Chemistry, 2008, vol. 80, No. 22, 8649-8655.

(56) References Cited

OTHER PUBLICATIONS

Jackson et al., "From homoligand- to mixed-ligand- monolayer-protected metal nanoparticles: a scanning tunneling microscopy investigation," Journal of the American Chemical Society, 2006, vol. 128, Issue 34, 11135-11149.

Miguel et al., "Comparative analysis of the 1H NMR relaxation enhancement produced by iron oxide and core-shell iron—iron oxide nanoparticles," Magnetic Resonance Imaging, 2007, vol. 25, Issue 10, 1437-1441.

Chen et al., "Chitosan/b-lactoglobulin core-shell nanoparticles as nutraceutical carriers," Biomaterials, 2005, vol. 26, Issue 30, 6041-6053.

Chang et al., "Protease activated quantum dot probes," Biochemical and Biophysical Research Communications, 2005, vol. 334, No. 4, 1317-1321.

Kircher et al., "Ratio Imaging of Enzyme Activity Using Dual Wavelength Optical Reporters," 2002, Molecular Imaging, vol. 1, No. 2, 89-95.

Schellenberger et al., "Protease-Specific Nanosensors for Magnetic Resonance Imaging," Bioconjugate Chem., American Chemical Society, 2008, No. 19, No. 12, 2440-2445.

Balivada et al., "A/C magnetic hyperthermia of melanoma mediated by iron(0)/iron oxide core/shell magnetic nanoparticies: a mouse study," BMC Cancer, 2010, vol. 10, No. 1, 119.

Wang et al., "Particle-based detection of DNA hybridization using electrochemical stripping measurements of an iron tracer," Analytica Chimica Acta, 2003, vol. 482, No. 2, 149-155.

Zeng et al., "Fe/Fe oxide nanocomposite particles with large specific absorption rate for hyperthermia," Applied Physics Letters, 2007, vol. 90, No. 23, 233112-1-233112-3.

The Patent Examination Report No. 1 dated Sep. 20, 2013 in the corresponding Australian Patent Application No. 2009221976 filed on Mar. 3, 2009.

Kim, Y.-P "Chip-Based Protease Assay Using Fluorescence Resonance Energy Transfer Between Quantum Dots and Fluorophores," Biochip Journal, Dec. 2007, 228-233, vol. 1, No. 4.

* cited by examiner

SEQUENCE LISTING

```
<160> NUMBER OF SEQ ID NOS: 57

<210> SEQ ID NO 1
<211> LENGTH: 10
<212> TYPE: PRT
<213> ORGANISM: Homo sapiens

<400> SEQUENCE: 1

Ser Arg Ser Arg Ser Arg Ser Arg Ser Arg
1               5                   10

<210> SEQ ID NO 2
<211> LENGTH: 5
<212> TYPE: PRT
<213> ORGANISM: Homo sapiens

<400> SEQUENCE: 2

Ser Gly Arg Ser Ala
1               5

<210> SEQ ID NO 3
<211> LENGTH: 8
<212> TYPE: PRT
<213> ORGANISM: Homo sapiens

<400> SEQUENCE: 3

Val Pro Met Ser Met Arg Gly Gly
1               5

<210> SEQ ID NO 4
<211> LENGTH: 8
<212> TYPE: PRT
<213> ORGANISM: Homo sapiens

<400> SEQUENCE: 4

Ile Pro Val Ser Leu Arg Ser Gly
1               5

<210> SEQ ID NO 5
<211> LENGTH: 8
<212> TYPE: PRT
<213> ORGANISM: Homo sapiens

<400> SEQUENCE: 5

Arg Pro Phe Ser Met Ile Met Gly
1               5

<210> SEQ ID NO 6
<211> LENGTH: 8
<212> TYPE: PRT
<213> ORGANISM: Homo sapiens

<400> SEQUENCE: 6
```

```
Val Pro Leu Ser Leu Thr Met Gly
1               5
```

```
<210> SEQ ID NO 7
<211> LENGTH: 8
<212> TYPE: PRT
<213> ORGANISM: Homo sapiens

<400> SEQUENCE: 7

Val Pro Leu Ser Leu Tyr Ser Gly
1               5
```

```
<210> SEQ ID NO 8
<211> LENGTH: 8
<212> TYPE: PRT
<213> ORGANISM: Homo sapiens

<400> SEQUENCE: 8

Ile Pro Glu Ser Leu Arg Ala Gly
1               5
```

```
<210> SEQ ID NO 9
<211> LENGTH: 11
<212> TYPE: PRT
<213> ORGANISM: Homo sapiens

<400> SEQUENCE: 9

Ser Gly Ser Pro Ala Phe Leu Ala Lys Asn Arg
1               5                   10
```

```
<210> SEQ ID NO 10
<211> LENGTH: 4
<212> TYPE: PRT
<213> ORGANISM: Homo sapiens

<400> SEQUENCE: 10

Asp Ala Phe Lys
1
```

```
<210> SEQ ID NO 11
<211> LENGTH: 10
<212> TYPE: PRT
<213> ORGANISM: Homo sapiens

<400> SEQUENCE: 11

Ser Gly Lys Pro Ile Leu Phe Phe Arg Leu
1               5                   10
```

```
<210> SEQ ID NO 12
<211> LENGTH: 10
<212> TYPE: PRT
<213> ORGANISM: Homo sapiens

<400> SEQUENCE: 12

Ser Gly Lys Pro Ile Ile Phe Phe Arg Leu
1               5                   10
```

```
<210> SEQ ID NO 13
<211> LENGTH: 8
<212> TYPE: PRT
<213> ORGANISM: Homo sapiens

<400> SEQUENCE: 13

Gly Pro Leu Gly Met Leu Ser Gln
```

```
<210> SEQ ID NO 14
<211> LENGTH: 4
<212> TYPE: PRT
<213> ORGANISM: Homo sapiens

<400> SEQUENCE: 14

Gly Gly Gly Cys
1

<210> SEQ ID NO 15
<211> LENGTH: 4
<212> TYPE: PRT
<213> ORGANISM: Homo sapiens

<400> SEQUENCE: 15

Ala Ala Ala Cys
1

<210> SEQ ID NO 16
<211> LENGTH: 4
<212> TYPE: PRT
<213> ORGANISM: Homo sapiens

<400> SEQUENCE: 16

Ser Ser Ser Cys
1

<210> SEQ ID NO 17
<211> LENGTH: 4
<212> TYPE: PRT
<213> ORGANISM: Homo sapiens

<400> SEQUENCE: 17

Thr Thr Thr Cys
1

<210> SEQ ID NO 18
<211> LENGTH: 19
<212> TYPE: PRT
<213> ORGANISM: Homo sapiens

<400> SEQUENCE: 18

Ser Arg Ser Arg Ser Arg Ser Arg Ser Arg Ser Gly Arg Ser Ala Gly
1               5                   10                  15

Gly Gly Cys

<210> SEQ ID NO 19
<211> LENGTH: 11
<212> TYPE: PRT
<213> ORGANISM: Homo sapiens

<400> SEQUENCE: 19

Lys Ser Arg Ser Arg Ser Arg Ser Arg Ser Arg
1               5                   10

<210> SEQ ID NO 20
<211> LENGTH: 12
<212> TYPE: PRT
<213> ORGANISM: Homo sapiens

<400> SEQUENCE: 20

Lys Lys Ser Arg Ser Arg Ser Arg Ser Arg Ser Arg
```

```
<210> SEQ ID NO 21
<211> LENGTH: 20
<212> TYPE: PRT
<213> ORGANISM: Homo sapiens

<400> SEQUENCE: 21

Lys Ser Arg Ser Arg Ser Arg Ser Arg Ser Gly Arg Ser Ala
1               5                   10                  15

Gly Gly Gly Cys
            20

<210> SEQ ID NO 22
<211> LENGTH: 21
<212> TYPE: PRT
<213> ORGANISM: Homo sapiens

<400> SEQUENCE: 22

Lys Lys Ser Arg Ser Arg Ser Arg Ser Arg Ser Gly Arg Ser
1               5                   10                  15

Ala Gly Gly Gly Cys
            20

<210> SEQ ID NO 23
<211> LENGTH: 4
<212> TYPE: PRT
<213> ORGANISM: Homo sapiens

<400> SEQUENCE: 23

Cys Gly Gly Gly
1

<210> SEQ ID NO 24
<211> LENGTH: 4
<212> TYPE: PRT
<213> ORGANISM: Homo sapiens

<400> SEQUENCE: 24

Lys Gly Gly Gly
1

<210> SEQ ID NO 25
<211> LENGTH: 31
<212> TYPE: PRT
<213> ORGANISM: Homo sapiens

<400> SEQUENCE: 25

His Gly Pro Glu Gly Leu Arg Val Gly Phe Tyr Glu Ser Asp Val Met
1               5                   10                  15

Gly Arg Gly His Ala Arg Leu Val His Val Glu Glu Pro His Thr
            20                  25                  30

<210> SEQ ID NO 26
<211> LENGTH: 12
<212> TYPE: PRT
<213> ORGANISM: Homo sapiens

<400> SEQUENCE: 26

Gly Pro Gln Gly Leu Ala Gly Gln Arg Gly Ile Val
1               5                   10

<210> SEQ ID NO 27
```

```
<211> LENGTH: 12
<212> TYPE: PRT
<213> ORGANISM: Homo sapiens

<400> SEQUENCE: 27

Ser Leu Leu Lys Ser Arg Met Val Pro Asn Phe Asn
1               5                   10

<210> SEQ ID NO 28
<211> LENGTH: 12
<212> TYPE: PRT
<213> ORGANISM: Homo sapiens

<400> SEQUENCE: 28

Ser Leu Leu Ile Phe Arg Ser Trp Ala Asn Phe Asn
1               5                   10

<210> SEQ ID NO 29
<211> LENGTH: 12
<212> TYPE: PRT
<213> ORGANISM: Homo sapiens

<400> SEQUENCE: 29

Ser Gly Val Val Ile Ala Thr Val Ile Val Ile Thr
1               5                   10

<210> SEQ ID NO 30
<211> LENGTH: 13
<212> TYPE: PRT
<213> ORGANISM: Homo sapiens

<400> SEQUENCE: 30

Lys Gly Gly Val Pro Met Ser Met Arg Gly Gly Gly Cys
1               5                   10

<210> SEQ ID NO 31
<211> LENGTH: 13
<212> TYPE: PRT
<213> ORGANISM: Homo sapiens

<400> SEQUENCE: 31

Lys Gly Gly Ile Pro Val Ser Leu Arg Ser Gly Gly Cys
1               5                   10

<210> SEQ ID NO 32
<211> LENGTH: 13
<212> TYPE: PRT
<213> ORGANISM: Homo sapiens

<400> SEQUENCE: 32

Lys Gly Gly Val Pro Leu Ser Leu Thr Met Gly Gly Cys
1               5                   10

<210> SEQ ID NO 33
<211> LENGTH: 13
<212> TYPE: PRT
<213> ORGANISM: Homo sapiens

<400> SEQUENCE: 33

Lys Gly Gly Gly Ser Gly Arg Ser Ala Gly Gly Gly Cys
1               5                   10

<210> SEQ ID NO 34
<211> LENGTH: 12
<212> TYPE: PRT
```

<213> ORGANISM: Homo sapiens

<400> SEQUENCE: 34

Cys Gly Gly Gly Ser Gly Arg Ser Ala Gly Gly Cys
1               5                   10

<210> SEQ ID NO 35
<211> LENGTH: 13
<212> TYPE: PRT
<213> ORGANISM: Homo sapiens

<400> SEQUENCE: 35

Cys Gly Gly Gly Ser Gly Arg Ser Ala Gly Gly Gly Cys
1               5                   10

<210> SEQ ID NO 36
<211> LENGTH: 11
<212> TYPE: PRT
<213> ORGANISM: Homo sapiens

<400> SEQUENCE: 36

Asp Gly Gly Ser Gly Arg Ser Ala Gly Gly Lys
1               5                   10

<210> SEQ ID NO 37
<211> LENGTH: 3
<212> TYPE: PRT
<213> ORGANISM: Homo sapiens

<400> SEQUENCE: 37

Lys Gly Gly
1

<210> SEQ ID NO 38
<211> LENGTH: 3
<212> TYPE: PRT
<213> ORGANISM: Homo sapiens

<400> SEQUENCE: 38

Gly Gly Cys
1

<210> SEQ ID NO 39
<211> LENGTH: 3
<212> TYPE: PRT
<213> ORGANISM: Homo sapiens

<400> SEQUENCE: 39

Gly Gly Lys
1

<210> SEQ ID NO 40
<211> LENGTH: 2
<212> TYPE: PRT
<213> ORGANISM: Homo sapiens

<400> SEQUENCE: 40

Gly Cys
1

<210> SEQ ID NO 41
<211> LENGTH: 11
<212> TYPE: PRT
<213> ORGANISM: Homo sapiens

```
<400> SEQUENCE: 41

Lys Gly Gly Ser Gly Arg Ser Ala Gly Gly Asp
1               5                   10

<210> SEQ ID NO 42
<211> LENGTH: 3
<212> TYPE: PRT
<213> ORGANISM: Homo sapiens

<400> SEQUENCE: 42

Gly Gly Asp
1

<210> SEQ ID NO 43
<211> LENGTH: 7
<212> TYPE: PRT
<213> ORGANISM: Homo sapiens

<400> SEQUENCE: 43

Lys Gly Gly Val Pro Met Ser
1               5

<210> SEQ ID NO 44
<211> LENGTH: 6
<212> TYPE: PRT
<213> ORGANISM: Homo sapiens

<400> SEQUENCE: 44

Met Arg Gly Gly Gly Cys
1               5

<210> SEQ ID NO 45
<211> LENGTH: 7
<212> TYPE: PRT
<213> ORGANISM: Homo sapiens

<400> SEQUENCE: 45

Lys Gly Gly Ile Pro Val Ser
1               5

<210> SEQ ID NO 46
<211> LENGTH: 6
<212> TYPE: PRT
<213> ORGANISM: Homo sapiens

<400> SEQUENCE: 46

Leu Arg Ser Gly Gly Cys
1               5

<210> SEQ ID NO 47
<211> LENGTH: 7
<212> TYPE: PRT
<213> ORGANISM: Homo sapiens

<400> SEQUENCE: 47

Lys Gly Gly Val Pro Leu Ser
1               5

<210> SEQ ID NO 48
<211> LENGTH: 6
<212> TYPE: PRT
<213> ORGANISM: Homo sapiens

<400> SEQUENCE: 48
```

```
Leu Thr Met Gly Gly Cys
1               5

<210> SEQ ID NO 49
<211> LENGTH: 7
<212> TYPE: PRT
<213> ORGANISM: Homo sapiens

<400> SEQUENCE: 49

Lys Gly Gly Gly Ser Gly Arg
1               5

<210> SEQ ID NO 50
<211> LENGTH: 6
<212> TYPE: PRT
<213> ORGANISM: Homo sapiens

<400> SEQUENCE: 50

Ser Ala Gly Gly Gly Cys
1               5

<210> SEQ ID NO 51
<211> LENGTH: 7
<212> TYPE: PRT
<213> ORGANISM: Homo sapiens

<400> SEQUENCE: 51

Cys Gly Gly Gly Ser Gly Arg
1               5

<210> SEQ ID NO 52
<211> LENGTH: 5
<212> TYPE: PRT
<213> ORGANISM: Homo sapiens

<400> SEQUENCE: 52

Ser Ala Gly Gly Cys
1               5

<210> SEQ ID NO 53
<211> LENGTH: 6
<212> TYPE: PRT
<213> ORGANISM: Homo sapiens

<400> SEQUENCE: 53

Asp Gly Gly Ser Gly Arg
1               5

<210> SEQ ID NO 54
<211> LENGTH: 5
<212> TYPE: PRT
<213> ORGANISM: Homo sapiens

<400> SEQUENCE: 54

Ser Ala Gly Gly Lys
1               5

<210> SEQ ID NO 55
<211> LENGTH: 13
<212> TYPE: PRT
<213> ORGANISM: Homo sapiens

<400> SEQUENCE: 55

Ser Arg Ser Arg Ser Arg Ser Arg Ser Arg Ser Gly Arg
1               5                   10
```

```
<210> SEQ ID NO 56
<211> LENGTH: 6
<212> TYPE: PRT
<213> ORGANISM: Homo sapiens

<400> SEQUENCE: 56

Lys Gly Gly Ser Gly Arg
1               5

<210> SEQ ID NO 57
<211> LENGTH: 5
<212> TYPE: PRT
<213> ORGANISM: Homo sapiens

<400> SEQUENCE: 57

Ser Ala Gly Gly Asp
1               5
```

PROTEASE ASSAY

CROSS-REFERENCE TO RELATED APPLICATIONS

This application is the National Stage of International Application No. PCT/US2009/035875, filed Mar. 3, 2009, which claims the priority benefit of a provisional application entitled FLUORESCENT PROTEASE ASSAY, Ser. No. 61/067,891, filed Mar. 3, 2008, the disclosures of which are incorporated by reference herein in their entirety.

SEQUENCE LISTING

The following application contains a sequence listing in computer readable format (CRF), submitted as a text file in ASCII format entitled "40132-PCT," created on Feb. 25, 2009, as 9 KB. The contents of the CRF are hereby incorporated by reference.

BACKGROUND OF THE INVENTION

1. Field of the Invention

The present invention relates in general to diagnostic assays for detecting protease activity associated with cancer, correlation of diagnostic results with cancer prognosis, and methods of detecting the presence of a cancerous or precancerous cell.

2. Description of the Prior Art

Cancer prognosis is based upon the stage of the disease. The four major stages are initial mutations, cell survival and tumor progression, angiogenesis, and finally invasion or metastasis. One of the biggest challenges is that cancer is a disease of the body's own cells. Because of this, it is often very challenging to diagnose cancer until the disease is quite progressed. This also affects treatment efficiency, since the cancer cells have the same enzymes, replication equipment, structural features, etc. as healthy cells, treatments that delineate cancer cells from healthy cells are difficult to develop. This is why staging and treatment is usually based on the symptoms (i.e., the size of the tumor, whether lymph nodes contain cancer, and whether the cancer has spread from the original site to other parts of the body), rather than on specifically targeting the origin of the cancer.

More recently, a number of proteases have been associated with disease progression in cancer. Proteases are a class of enzyme that catalyze the cleavage of the peptide bond in other proteins. They can be very specific (only being able to degrade one peptide bond in one protein) or extremely broad (e.g., being able to cleave the peptide bond every time there is, for example, a lysine). Several proteases are known to be over-expressed by various cancer cell lines. Proteases that are known to be necessary for cancer development and progression include Matrix Metalloproteinases (MMPs), Tissue Serine Proteases, and the Cathepsins. Many of these proteases are either upregulated in the cancer cells (that is, they have a much higher activity in the tumor than in healthy tissue), mis-expressed (that is, they are found in compartments where they should not be found), or are involved in embryonic development, but should not be found to any significant extent in an adult cells.

MMPs are the classic cancer-associated proteases. MMPs are a family of zinc proteases that are named for the zinc and calcium ions that are required as cofactors. There are 21 different known MMPs that are grouped into families based on their substrates: collagenases, gelatinases, stromelysins, matrilysin, metalloelastase, enamelysin, and membrane-type MMPs. As can be seen from the family names, MMPs degrade the proteins that make up the extracellular matrix (ECM) and the basement membrane (BM) of tissue. MMPs are usually not produced by the cancerous cells themselves, but by the stromal cells surrounding the tumor. This is because the cancerous cells give off a variety of cell signals that cause the surrounding stromal cells to highly upregulate their production of MMPs. MMPs are vital to cancer survival and progression for several reasons. First, they cleave cell surface bound growth factors from the stromal and epithelial cells and release them to interact with the cancer cells to stimulate growth. They also play a role in angiogenesis by opening the ECM to new vessel development as well as by releasing pro-angiogenic factors and starting pro-angiogenic protease cascades. MMPs play a major role in tumor metastasis by degrading the ECM and the BM, allowing the cells to pass through tissue barriers. They also release ECM and BM fragments, which stimulates cell movement.

Several serine proteases have well-documented roles in cancer as well, especially urokinase plasminogen activator (uPA) and plasmin. Elevated expression levels of urokinase and several other components of the plasminogen activation system have been found to be correlated with tumor malignancy. uPA is a very specific protease that binds to its receptor, uPAR, and cleaves the inactive plasminogen (a zymogen) to the active plasmin. This is the first step in a well-known cascade that causes angiogenesis. It is believed that the tissue degradation that follows plasminogen activation facilitates tissue invasion and contributes to metastasis.

Cathepsins, with a few exceptions, are cysteine proteases. Often found in the lysosomal/endosomal pathway, cathepsins usually operate at low pH values, but some are still active at neutral pH. Three of the cathepsins, B, D, and L, are active at neutral pH and are often misexpressed in cancer, causing activation outside of the cells. This activation outside of the cell can cause ECM degradation.

Many studies directed to assess the prognostic impact of the plasminogen/plasmin components have been conducted, mostly based on antigen level quantitation in tissue extracts from surgically removed tumors. These values have been subsequently correlated with prognosis in several types of cancers. However, determining ways to distinguish cancerous cells from healthy cells remains a large area of research in cancer therapy, and there is still a need in the art for methods of quantitatively detecting cancer progression and stages of the disease that can be applied in vitro and in vivo. There is also a need for detecting multiple markers of the various cancer stages at one time without the need for separate tests. There also is a need for in vivo characterization of cancer, so that treatment can be directed to the most malignant cancer tissue.

SUMMARY OF THE INVENTION

The present invention provides a nanoplatform assembly for detecting protease activity comprising a first particle, a second particle, and a linkage between the first and second particles, wherein the linkage comprises a protease consensus sequence.

The invention also provides a composition comprising a diagnostic assay for assessing the activity of a protease and a pharmaceutically-acceptable carrier. The diagnostic assay includes the nanoplatform assembly comprising a first particle, a second particle, and a linkage between the first and second particles, wherein the linkage comprises a consensus sequence specific to the protease.

In addition, the invention provides a method for detecting the activity of a protease associated with a cancerous or precancerous cell in a mammal. The method comprises contacting a fluid sample from the mammal with a diagnostic assay. The diagnostic assay comprises a nanoplatform assembly, the nanoplatform assembly comprising a first particle, a second particle, and a linkage between the first and second particles, wherein the linkage comprises a consensus sequence specific to the protease. The assay is exposed to an energy source to excite the assay. The changes in the absorption or emission spectrum of the assay are then detected. These changes correspond to protease activity.

The invention provides a further method for detecting the activity of a protease associated with a cancerous or precancerous cell in a mammal. The inventive method comprises administering to the mammal a composition comprising the inventive diagnostic assay for assessing the activity of a protease and a pharmaceutically-acceptable carrier. The assay in composition is then activated. The region of the mammal suspected of having a cancerous or precancerous cell is exposed to an energy source, which excites the assay, and the changes in the absorption or emission spectrum of the assay are detected. These changes correspond to protease activity, which can then be correlated with a prognosis for cancer progression.

DETAILED DESCRIPTION OF THE PREFERRED EMBODIMENTS

Figure 1:
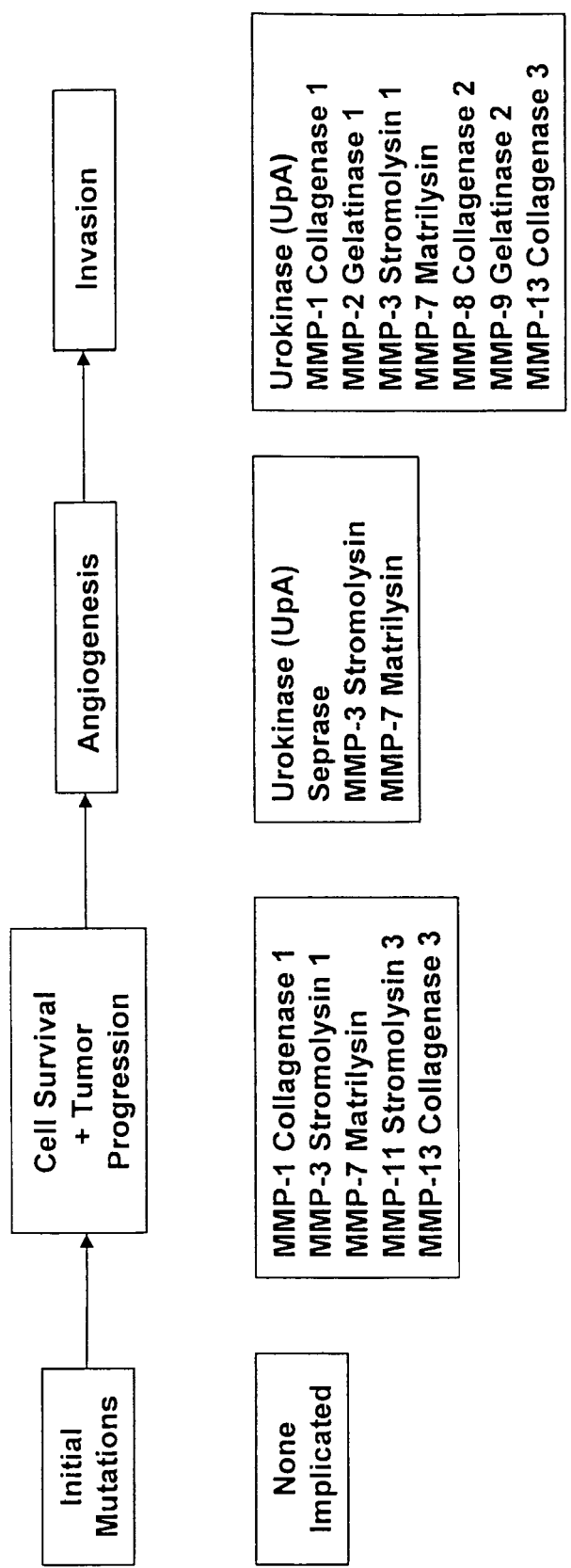
FIG. 1 depicts the four main stages of cancer progression and the proteases associated with these stages.

It has been found that the presence of certain proteases can serve as a marker for the ability of many cancers to grow and eventually metastasize. The present invention provides diagnostic assays and methods of detecting protease activity and diagnosing corresponding disease progression. The inventive assays can be used to detect any protease or enzyme that cleaves a DNA-, RNA-, carbohydrate-, or protein-based linker.

The diagnostic assays of the invention comprise a nanoplatform assembly. The nanoplatform assembly is comprised of a protease consensus sequence (the sequence of amino acids cleaved by the protease), which is used as a linker between two particles. More preferably, the linker is comprised of an oligopeptide containing the consensus sequence.

Oligopeptide Linkages and Consensus Sequences

Suitable oligopeptides will comprise a terminal carboxylic acid group (C terminus) and a terminal amine group (N terminus). The oligopeptide also preferably comprises a thiol group at the C terminus, although this may be modified depending upon the particles used in the nanoplatform assembly. More preferably, the oligopeptide linker comprises a hydrophilic region of at least 10 amino acids N-terminal to the protease consensus sequence, and a linking region C-terminal to the cleavage sequence, wherein the C-terminal linking region comprises a thiol reactive group at its terminus. Even more preferably, the C terminus of the oligopeptide comprises a cysteine residue, lysine, or aspartate. The N-terminal hydrophilic region of the oligopeptide preferably has an excess positive or negative charge at a ratio of about 1:1. The N-terminal hydrophilic region also preferably comprises amino acid residues capable of forming hydrogen bonds with each other.

Particularly preferred C-terminal linking regions comprise a sequence selected from the group consisting of GGGC (SEQ ID NO: 14), AAAC (SEQ ID NO: 15), SSSC (SEQ ID NO: 16), TTTC (SEQ ID NO: 17), GGC (SEQ ID NO: 38), GGK (SEQ ID NO: 39), GC (SEQ ID NO: 40), and GGD (SEQ ID NO: 42). Particularly preferred N-terminal regions of the oligopeptide comprise a sequence selected from the group consisting of SRSRSRSRSR (SEQ ID NO: 1), KSRSRSRSRSR (SEQ ID NO: 19), KKSRSRSRSRSR (SEQ ID NO: 20), CGGG (SEQ ID NO: 23), KGGG (SEQ ID NO: 24), and KGG (SEQ ID NO: 37). The N-terminus preferably further comprises at least one terminal group selected from the group consisting of lysine, ornithine, 2,4 diaminobutyric acid, and 2,3 diaminoproprionic acid. Another preferred oligopeptide has the following general structure:

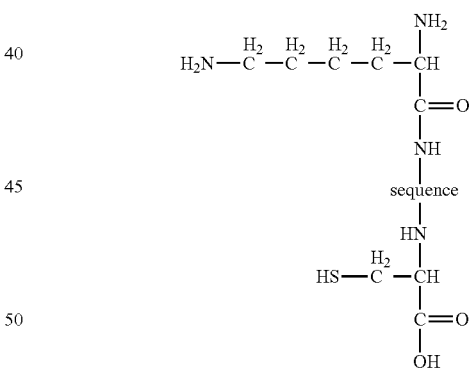

where the "sequence" can be any of the oligopeptide or consensus sequences described herein. The oligopeptides can be purchased, or they can be synthesized using known methods (e.g., modified Merrifield synthesis).

Preferably, the consensus sequence used in the inventive diagnostic assays is selected from the group consisting of serine protease cleavage sequences, aspartyl protease cleavage sequences, cysteine protease cleavage sequences, and metalloprotease cleaveage sequences. Even more preferably, the consensus sequence comprises a cleavage sequence for a protease selected from the group consisting of urokinase, matrix metallopeptidase, cathepsin, and gelatinase. Particularly preferred proteases and their corresponding consensus sequences are listed in Table I below.

TABLE I

| Protease | Consensus Sequence (Cleavage Sequence) |
|---|---|
| MMP-1 | VPMSMRGG (SEQ ID NO: 3) |
| MMP-2 | IPVSLRSG (SEQ ID NO: 4) |
| MMP-3 | RPFSMIMG (SEQ ID NO: 5) |
| MMP-7 | VPLSLTMG (SEQ ID NO: 6) |
| MMP-9 | VPLSLYSG (SEQ ID NO: 7) |
| MMP-11 | HGPEGLRVGFYESDVMGRGHARLVHVEEPHT (SEQ ID NO: 25) |
| MMP-13 | GPQGLAGQRGIV (SEQ ID NO: 26) |
| MT1-MMP | IPESLRAG (SEQ ID NO: 8) |
| uPA | SGRSA (SEQ ID NO: 2) |
| Cathepsin B | SLLKSRMVPNFN (SEQ ID NO: 27) DAFK (SEQ ID NO: 10) |
| Cathepsin D | SLLIFRSWANFN (SEQ ID NO: 28) SGKPILFFRL (SEQ ID NO: 11) |
| Cathepsin E | SGSPAFLAKNR (SEQ ID NO: 9) SGKPIIFFRL (SEQ ID NO: 12) |
| Cathepsin L | SGVVIATVIVIT (SEQ ID NO: 29) |
| Gelatinase | GPLGMLSQ (SEQ ID NO: 13) |

With reference to FIG. 1, the foregoing proteases are associated with many specific events in cancer progression. The stages of disease progression are separated into four events: initial mutation, cell survival/tumor progression, angiogenesis (development of new blood vessels), and invasion/tissue remodeling. The array of proteases associated with each stage can give a good picture of how far the cancer has progressed and what the prognosis will be. The preferred diagnostic reagents or assays comprise a protease consensus sequence for a protease selected from the group consisting of uPA, MMP-1, MMP-2, and MMP-7. The most preferred oligopeptide sequences for detecting uPA, MMP-1, MMP-2, and MMP-7, respectively, are listed in the table below with the point of cleavage indicated by "-".

TABLE II

| Protease | Preferred Oligopeptide with Consensus Sequence |
|---|---|
| MMP-1 | KGGVPMS-MRGGGC (SEQ ID NO: 30) |
| MMP-2 | KGGIPVS-LRSGGC (SEQ ID NO: 31) |
| MMP-7 | KGGVPLS-LTMGGC (SEQ ID NO: 32) |
| uPA | KGGGSGR-SAGGGC (SEQ ID NO: 33) CGGGSGR-SAGGC (SEQ ID NO: 34) CGGGSGR-SAGGGC (SEQ ID NO: 35) DGGSGR-SAGGK (SEQ ID NO: 36) SRSRSRSRSRSGR-SAGGGC (SEQ ID NO: 18) KGGSGR-SAGGD (SEQ ID NO: 41) |

With reference again to FIG. 1, an accurate cancer prognosis can be determined using the inventive assays. In particular, if MMP-1 and MMP-7, but neither of the other two proteases are detected by the inventive assays, the cancer prognosis is for cell survival/tumor progression. If uPA and MMP-7 are detected by the assays (but not MMP-1 or MMP-2), the prognosis is for angiogenesis. If all four proteases are detected, the prognosis is for invasion and eventual metastasis. Thus, the in-vivo measurements of these four proteases enable the spatially resolved determination of the progression of cancerous tissue, and permit a more detailed prognosis that can guide the treatment towards the most active tumors in the body.

In the presence of the protease, the consensus sequence of the nanoplatform assembly is cleaved, and the spectral change caused by this cleavage is detected by the inventive assays. Thus, depending upon the proteases targeted by the nanoplatform, two or more of the following sequences will result: KGGVPMS (SEQ ID NO: 43), MRGGGC (SEQ ID NO: 44), KGGIPVS (SEQ ID NO: 45), LRSGGC (SEQ ID NO: 46), KGGVPLS (SEQ ID NO: 47), LTMGGC (SEQ ID NO: 48), KGGGSGR (SEQ ID NO: 49), SAGGGC (SEQ ID NO: 50), CGGGSGR (SEQ ID NO: 51), SAGGC (SEQ ID NO: 52), DGGSGR (SEQ ID NO: 53), SAGGK (SEQ ID NO: 54), SRSRSRSRSRSGR (SEQ ID NO: 55), KGGSGR (SEQ ID NO: 56), or SAGGD (SEQ ID NO: 57).

Particles for Assay

A number of different types of particles can be used to form the nanoplatform assemblies for use in the inventive assays, depending upon the type of sensor used to measure the protease activity, as discussed in more detail below. Preferably, the excitation and emission spectral maxima of the particles are between 650 and 800 nm. Preferred particles for use in the diagnostic assays are selected from the group consisting of nanoparticles (e.g., metal, metal alloy, or core/shell), chromophores/luminophores, quantum dots, viologens, and combinations thereof.

1. Nanoparticles

The term "nanoparticle" as used herein refers to metal nanocrystalline particles that can optionally be surrounded by a metal or nonmetal nanolayer shell. Suitable nanoparticles preferably have a diameter of from about 1 nm to about 100 nm, more preferably from about 10 nm to about 50 nm, and even more preferably from about 5 nm to about 20 nm. The nanoparticles can comprise any type of metal (including elemental metal) or metal alloy. Preferably, the metal or metal alloy nanoparticles comprise a metal selected from the group consisting of gold (Au), silver (Ag), copper (Cu), nickel (Ni), palladium (Pd), platinum (Pt), cobalt (Co), rhodium (Rh), iridium (Ir), iron (Fe), ruthenium (Ru), osmium (Os), manganese (Mn), rhenium (Re), scandium (Sc), titanium (Ti), vanadium (V), chromium (Cr), zinc (Zn), yttrium (Y), zirconium (Zr), niobium (Nb), molybdenum (Mo), technetium (Tc), cadmium (Cd), lanthanum (La), lutetium (Lu), hafnium (Hf), tantalum (Ta), tungsten (W), actinium (Ac), lawrencium (Lr), rutherfordium (Rf), dubnium (Db), seaborgium (Sg), bohrium (Bh), Hassium (Hs), meitnerium (Mt), darmstadtium (Ds), roentgenium (Rg), ununbium (Uub), selenium (Se), and the oxides (e.g., FeO, $Fe_3O_4$, $Fe_2O_3$, $Fe_xO_y$ (non-stoichiometric iron oxide), CuO, NiO, $Ag_2O$, $Mn_2O_3$), hydroxides, sulfides, selenides, and tellurides of the foregoing, and combinations thereof.

Core/shell nanoparticles preferably comprise a metal or metal alloy core and a metal shell. Preferred cores are selected from the group consisting of Au, Ag, Cu, Co, Fe, and Pt. Preferred shells are selected from the group consisting of Au, Ag, Cu, Co, Fe, Pt, the metal oxides thereof, and combinations thereof. Particularly preferred metal core/shell combinations are selected from the group consisting of Fe/Au, $Fe/Fe_3O_4$, and $Au/Fe_2O_3$. The core of the nanoparticle preferably has a diameter of from about 1 nm to about 25 nm, and more preferably from about 3 nm to about 5 nm. The metal shell of the core/shell nanoparticle preferably has a thickness of from about 0.5 nm to about 10 nm, and more preferably from about 0.5 to about 2 nm.

The nanoparticles can be stabilized or non-stabilized. Stabilized nanoparticles preferably comprise an organic monolayer surrounding the nanoparticle core. The term "stabilized" as used herein means the use of a ligand shell or monolayer to coat, protect (e.g., from bio-corrosion), or impart properties (e.g., water solubility) to, the nanoparticle. The monolayer can be comprised of several of the same ligands (i.e., homoligand) or of mixed ligands. Various techniques for attaching ligands to the surface of various nanoparticles are known in the art. For example, nanoparticles may be mixed in a solution containing the ligands to promote the coating of the nanoparticle. Alternatively, coatings may be applied to nanoparticles by exposing the nanoparticles to a vapor phase of the coating material such that the coating attaches to or bonds with the nanoparticle. Preferably, the ligands attach to the nanoparticle through covalent bonding. The number of ligands required to form a monolayer will be dependent upon the size of the nanoparticle.

The ligands comprise functional groups that are attracted to the nanoparticle's metal surface. Preferably, the ligands comprise at least one group selected from the group consisting of thiols, alcohols, nitro compounds, phosphines, phosphine oxides, resorcinarenes, selenides, phosphinic acids, phosphonicacids, sulfonic acids, sulfonates, carboxylic acids, disulfides, peroxides, amines, nitriles, isonitriles, thionitiles, oxynitriles, oxysilanes, alkanes, alkenes, alkynes, aromatic compounds, and seleno moieties. Preferred organic monolayers are selected from the group consisting of alkanethiolate monolayers, aminoalkylthiolate monolayers, alkylthiolsulfate monolayers, and organic phenols (e.g., dopamine and derivatives thereof). The thickness of the organic monolayer is preferably less than about 10 nm, and more preferably less than about 5 nm. Particularly preferred stabilized nanoparticles are selected from the group consisting of trioctyl-phosphinoxide-stabilized nanoparticles, amine-stabilized nanoparticles, carboxylic-acid-stabilized nanoparticles, phosphine-stabilized nanoparticles, thiol-stabilized nanoparticles, aminoalkylthiol-stabilized nanoparticles, and organic phenol-stabilized nanoparticles.

2. Chromophores/Luminophores

Chromophore/luminophore particles suitable for use in the inventive assays include any organic or inorganic dyes, fluorophores, phosphophores, light absorbing nanoparticles (e.g., Au, Ag, Pt, Pd), combinations thereof, or the metalated complexes thereof. Preferably, the chromophore/luminophore particles have a size of less than about 100 nm.

Suitable organic dyes are selected from the group consisting of coumarins, pyrene, cyanines, benzenes, N-methylcarbazole, erythrosin B, N-acetyl-L-tryptophanamide, 2,5-diphenyloxazole, rubrene, and N-(3-sulfopropyl)acridinium. Specific examples of preferred coumarins include 7-aminocoumarin, 7-dialkylamino coumarin, and coumarin 153. Examples of preferred benzenes include 1,4-bis(5-phenyloxazol-2-yl)benzene and 1,4-diphenylbenzene. Examples of preferred cyanines include oxacyanines, thiacyanines, indocyanins, merocyanines, and carbocyanines. Other exemplary cyanines include ECL Plus, ECF, C3-Oxacyanine, C3-Thiacyanine Dye (EtOH), C3-Thiacyanine Dye (PrOH), C5-Indocyanine, C5-Oxacyanine, C5-Thiacyanine, C7-Indocyanine, C7-Oxacyanine, CypHer5, Dye-33, Cy7, Cy5, Cy5.5, Cy3Cy5 ET, Cy3B, Cy3, Cy3.5, Cy2, CBQCA, NIR1, NIR2, NIR3, NIR4, NIR820, SNIR1, SNIR2, SNIR4, Merocyanine 540, Pinacyanol-Iodide, 1,1-Diethyl-4,4-carbocyanine iodide, Stains All, Dye-1041, or Dye-304.

Suitable inorganic dyes are selected from the group consisting of metalated and non-metalated porphyrins, phthalocyanines, chlorins (e.g., chlorophyll A and B), and metalated chromophores. Preferred porphyrins are selected from the group consisting of tetra carboxy-phenyl-porphyrin (TCPP) and Zn-TCPP. Preferred metalated chromophores are selected from the group consisting of ruthenium polypyridyl complexes, osmium polypyridyl complexes, rhodium polypyridyl complexes, 3-(1-methylbenzoimidazol-2-yl)-7-(diethylamino)-coumarin complexes of iridium(III), and 3-(benzothiazol-2-yl)-7-(diethylamino)-coumarin complexes with iridium(III).

Suitable fluorophores and phosphophores are selected from the group consisting of phosphorescent dyes, fluoresceines, rhodamines (e.g., rhodamine B, rhodamine 6G), and anthracenes (e.g., 9-cyanoanthracene, 9,10-diphenylanthracene, 1-Chloro-9,10-bis(phenylethynyl)anthracene).

3. Quantum Dots

A quantum dot is a semiconductor composed of atoms from groups II-VI or III-V elements of the periodic table (e.g., CdSe. CdTe, InP). The optical properties of quantum dots can be manipulated by synthesizing a (usually stabilizing) shell. Such quantum dots are known as core-shell quantum dots (e.g., CdSe/ZnS, InP/ZnS, InP/CdSe). Quantum dots of the same material, but with different sizes, can emit light of different colors. Their brightness is attributed to the quantization of energy levels due to confinement of an electron in all three spatial dimensions. In a bulk semiconductor, an electron-hole pair is bound within the Bohr exciton radius, which is characteristic for each type of semiconductor. A quantum dot is smaller than the Bohr exciton radius, which causes the appearance of discrete energy levels. The band gap, $\Delta E$, between the valance and conduction band of the semiconductor is a function of the nanocrystal's size and shape. Quantum dots feature slightly lower luminescence quantum yields than traditional organic fluorophores but they have much larger absorption cross-sections and very low rates of photobleaching. Molar extinction coefficients of quantum dots are about $10^5$-$10^6$ $M^{-1}$ $cm^{-1}$, which is 10-100 times larger than dyes.

Core/shell quantum dots have higher band gap shells around their lower band gap cores, which emit light without any absorption by the shell. The shell passivates surface nonradiative emission from the core thereby enhancing the photoluminescence quantum yield and preventing natural degradation. The shell of type I quantum dots (e.g. CdSe/ZnS) has a higher energy conduction band and a lower energy valance band than that of the core, resulting in confinement of both electron and hole in the core. The conduction and valance bands of the shell of type II quantum dots (e.g., CdTe/CdSe, CdSe/ZnTe) are either both lower or both higher in energy than those of the core. Thus, the motions of the electron and the hole are restricted to one dimension. Radiative recombination of the exciton at the core-shell interface gives rise to the type-II emission. Type II quantum dots behave as indirect semiconductors near band edges and therefore, have an absorption tail into the red and near infrared. Alloyed semiconductor quantum dots (CdSeTe) can also be used, although types I and II are most preferred. The alloy composition and internal structure, which can be varied, permits tuning the optical properties without changing the particles' size. These quantum dots can be used to develop near infrared fluorescent probes for in vivo biological assays as they can emit up to 850 nm.

Particularly preferred quantum dots are selected from the group consisting of CdSe/ZnS core/shell quantum dots, CdTe/CdSe core/shell quantum dots, CdSe/ZnTe core/shell quantum dots, and alloyed semiconductor quantum dots (e.g., CdSeTe). The quantum dots are preferably small enough to be discharged via the renal pathway when used in vivo. More preferably, the quantum dots are less than about 10 nm in diameter, even more preferably from about 2 nm to about 5.5 nm in diameter, and most preferably from about 1.5 nm to about 4.5 nm in diameter. If different color emission is needed for creating multiple sensors (multiplex detection), this can be achieved by changing the size of the quantum dot core yielding different emission wavelengths. The quantum dots can be stabilized or unstabilized as discussed above regarding nanoparticles. Preferred ligands for stabilizing quantum dots are resorcinarenes.

Nanoplatform Assemblies for Assays

The diagnostic nanoplatform assemblies comprise at least two particles linked together via the oligopeptide sequences discussed above. In addition, the assemblies can comprise multiple particles linked to a single central particle, depending upon the particles used and the spectrum used to detect the assay. If the whole visible and near IR spectrum are used during detection, up to ten particles can be linked to a central particle (for detecting up to 10 different proteases in a single assay, if different cleavage sequences are used to link each particle). If either the visible spectrum or IR spectrum is used alone, up to five particles can be linked to a central particle (for detecting up to 5 different proteases in a single assay, if different cleavage sequences are used to link each particle). The linkage between the particles, in addition to the oligopeptide sequence, can be further comprised of ligands or spacer moieties (discussed below) attached to either particle.

The assemblies can be comprised of the same type of particles (i.e., a nanoparticle linked to a nanoparticle), or of different particles (i.e., a nanoparticle linked to a different type of particle, such as a chromophore/luminophore or quantum dot). The assemblies can also be comprised of a chromophore/luminophore linked to a chromophore/luminophore. When two nanoparticles are used in the same diagnostic assembly, they can be identical (i.e., comprise the same kind of metal, alloy, or core/shell, and be the same shape (e.g., round, globular, rod-shaped, etc.)), or each particle can be different (i.e., non-identical, physically and/or chemically). Preferably, the particles have different chemical compositions and sizes, and the assemblies are created using different nanoparticles or chromophores/luminophores, or the assembly is created between a nanoparticle and a chromophore/luminophore (i.e., non-identical particles). In one aspect, the assemblies comprise two fluorophores separated by a distance that enables fluorescence resonance energy transfer or surface plasmon resonance between the two fluorophores. Each fluorophore comprises a fluorescent nanoparticle or a fluorescent organic dye, and are each bonded to a respective terminus of the oligopeptide linker that comprises the protease cleavage sequence.

The distance between the particles in the assembly will be dependent upon the length of the oligopeptide linker, as well as any ligands or spacers attached to either particle. However, the distance is preferably less than about 10 nm, more preferably less than about 5 nm, and even more preferably from about 1 nm to about 3 nm.

In the case of chromophores/luminophores, such particles are preferably covalently bonded to the oligopeptide linker, optionally, via a spacer moiety bound to the chromophore/luminophore. Depending upon which end of the oligopeptide the spacer will be linked to, preferred spacer moieties comprise reactive groups selected from the group consisting of carboxyls, thiols, and combinations thereof. In one preferred embodiment, the spacer moiety is covalently attached to the N-terminus of the oligopeptide linker through an amide bond. In an alternative embodiment, the spacer moiety is covalently attached to the C-terminus of the oligopeptide linker through a disulfide bond. Particularly preferred spacer moieties include ethylene glycols (preferably $C_3$-$C_{20}$, such as tetraethylene glycols to dodecaethylene glycols), amides (preferably $C_3$-$C_{20}$), alkylenes (preferably $C_3$-$C_{20}$), or esters (preferably $C_3$-$C_{20}$), each having two terminal carboxyl groups or a terminal carboxyl group and a terminal thiol group.

The diagnostic assays can be utilized as is, or can be part of a composition comprising the diagnostic assay and a pharmaceutically-acceptable carrier. For in vivo diagnostics, the assays will preferably be delivered using a pharmaceutically-acceptable carrier. A suitable example includes traditional liposomal delivery, discussed in more detail below.

The assays can be used to detect cancerous or pre-cancerous cells associated with a cancer selected from the group consisting of an AIDS-related cancer, AIDS-related lymphoma, anal cancer, appendix cancer, childhood cerebellar astrocytoma, childhood cerebral astrocytoma, basal cell carcinoma, extrahepatic bile duct cancer, childhood brain stem glioma, adult brain tumor, childhood malignant glioma, childhood ependymoma, childhood medulloblastoma, childhood supratentorial primitive neuroectodermal tumors, childhood visual pathway and hypothalamic glioma, breast cancer, pregnancy-related breast cancer, childhood breast cancer, male breast cancer, childhood carcinoid tumor, gastrointestinal carcinoid tumor, primary central nervous system lymphoma, cervical cancer, colon cancer, childhood colorectal cancer, esophageal cancer, childhood esophageal cancer, intraocular melanoma, retinoblastoma, adult glioma, adult (primary) hepatocellular cancer, childhood (primary) hepatocellular cancer, adult Hodgkin lymphoma, childhood Hodgkin lymphoma, islet cell tumors, Kaposi Sarcoma, kidney (renal cell) cancer, childhood kidney cancer, adult (primary) liver cancer, childhood (primary) liver cancer, Non-small cell liver cancer, small cell liver cancer, AIDS-related lymphoma, Burkitt lymphoma, adult Non-Hodgkin lymphoma, childhood Non-Hodgkin lymphoma, primary central nervous system lymphoma, melanoma, adult malignant mesothelioma, childhood mesothelioma, metastatic squamous neck cancer with occult primary, mouth cancer, childhood multiple endocrine neoplasia syndrome, multiple myeloma/plasma cell neoplasm, mycosis fungoides, myelodysplastic syndromes, myelodysplastic/myeloproliferative diseases, adult acute myeloid leukemia, childhood acute myeloid leukemia, multiple myeloma, neuroblastoma, non-small cell lung cancer, childhood ovarian cancer, ovarian epithelial cancer, ovarian germ cell tumor, ovarian low malignant potential tumor, pancreatic cancer, childhood pancreatic cancer, islet cell pancreatic cancer, parathyroid cancer, penile cancer, plasma cell neoplasm/multiple myeloma, pleuropulmonary blastoma, prostate cancer, rectal cancer, childhood renal cell cancer, renal pelvis and ureter, transitional cell cancer, adult soft tissue sarcoma, childhood soft tissue sarcoma, uterine sarcoma, skin cancer (nonmelanoma), childhood skin cancer, melanoma, Merkel cell skin carcinoma, small cell lung cancer, small intestine cancer, squamous cell carcinoma, stomach cancer, childhood stomach cancer, cutaneous T-Cell lymphoma, testicular cancer, thyroid cancer, childhood thyroid cancer, and vaginal cancer.

The Inventive Methods

One advantage of the inventive assays is the flexibility to adapt the assays by modifying the particles to suit the sensor technology available, and likewise, using a variety of sensor technologies for detecting enzyme activity depending upon the particles available.

1. FRET-Based Sensors

In one aspect of the invention, the assays work on the basis of surface plasmon resonance and Förster resonance energy transfer (FRET) between non-identical particles, such as particles having different chemical compositions or sizes, or between different chromophores/luminophores, or between a nanoparticle and a chromophore/luminophore, linked by the cleavage sequences. FRET describes energy transfer between two particles. Surface plasmon resonance is used to excite the particles. A donor particle initially in its excited state, may transfer this energy to an acceptor particle in close proximity through nonradiative dipole-dipole coupling. When both particles are fluorescent chromophores/luminophores, the term "fluorescence resonance energy transfer" is often used instead, although the energy is not actually transferred by fluorescence. In the present invention, FRET is used to detect protease cleavage. Briefly, while the particles are bound by the oligopeptide, emission from the acceptor is observed upon excitation of the donor particle. Once the enzyme cleaves the linkage between the particles, FRET change is observed, and the emission spectra changes. Only the donor emission is observed.

In more detail, if both particles are within the so-called Förster-distance, energy transfer occurs between the two particles and a red-shift in absorbance and emission is observed. During this ultrafast process, the energy of the electronically excited state or surface plasmon of the first particle is at least partially transferred to the second particle. Under these conditions, light is emitted from the second particle. However, once the bond between the two particles is cleaved by the enzyme, light is emitted only from the first particle and a distinct blue-shift in absorption and emission is observed. This is because the distance between both particles greatly increases (see equation below).

The maximum of the observed plasmon resonance can be characterized by the following equation.

$$\frac{\Delta\lambda}{\lambda_0} \approx c\exp\frac{-(s/D)}{d}$$

where $\Delta\lambda/\lambda_0$ is the fractional plasmon shift, c and d are constants, s is the edge-to-edge distance between the particles, and D is the particle diameter. In the nanoplatform assemblies the distance separating the particles can be calculated to be about 0.3 nm per amino acid present in the oligopeptide. The FRET efficiency ("E") can be characterized as $$E = \frac{1}{1+\left(\frac{R}{R_0}\right)^6}$$

where $R_0$ is the Förster distance (i.e., the distance at which the donor transfers 50% of its energy to the acceptor via FRET). Both particles for use with the FRET assays can be chosen so that the absorption and emission wavelengths of each particle are distinctly different, and will therefore appear as distinct luminescent bands. Preferably, the assays can be performed in vitro and in vivo. Therefore, excitation of the first particle can preferably performed between about 400 nm and about 1000 nm, more preferably between about 500 nm to about 800 nm, and even more preferably between about 650 nm and about 800 nm in order to minimize absorption and scattering by human tissue for in vivo use. When using chromophore/luminophore particles, there is also preferably an overlap between the excitation spectrum of the first chromophore/luminophore and the fluorescence or phosphorescence spectrum of the second chromophore/luminophore to permit adequate Förster energy transfer.

a. In vitro Methods

The assays may be used to detect protease activity in a fluid sample comprising a biological fluid, such as urine or blood samples of a mammal. In one aspect, a urine sample is collected from the mammal and physically mixed with the assay. Preferably, the concentration of the assay in the urine is from about $1\times10^{-4}$ M to about $1\times10^{-10}$ M, and more preferably from about $1\times10^{-5}$ M to about $1\times10^{-8}$ M. Excitation is preferably performed with an energy source of appropriate wavelength selected from the group consisting of a tungsten lamp, laser diode, laser, and bioluminescence (e.g., luciferase, renilla, green fluorescent protein). The wavelength used will depend upon the particles used in the nanoplatform assembly. Preferably, the wavelength ranges between about 400 nm and about 1000 nm, and more preferably between about 500 nm and 800 nm. The changes in absorption and emission of the particles as the protease in the urine sample cleaves the oligopeptide linkers will be observed over a time period of from about 1 second to about 30 minutes, and preferably from about 30 seconds to about 10 minutes, when in the presence of an aggressive tumor. In the presence of the protease, a typical absorption and emission blue-shift of between about 5 and about 200 nm will be observed. Thus, in the inventive method, a blue-shift in absorption or emission spectrum maximum between 5 and 200 nm preferably indicates the presence of a cancerous or precancerous cell in the mammal.

Blood can be collected from the mammal and analyzed like urine discussed above. Preferably, the concentration of the assay in the blood sample is from about $1\times10^{-4}$ M to about $1\times10^{-10}$ M, and more preferably from about $1\times10^{-5}$ M to about $1\times10^{-8}$ M. The wavelength used will depend upon the particles used in the nanoplatform assembly. Preferably, the wavelength ranges between about 500 nm and about 1000 nm, and more preferably between about 600 nm and 800 nm. More preferably, excitation is performed using multi-photon excitation at a wavelength of about 800 nm with a Ti-sapphire-laser because of the strong self-absorption of blood. Changes in emission will be observed over a time period of from about 1 second to about 30 minutes, and preferably from about 30 seconds to about 10 minutes, when in the presence of an aggressive tumor. As with urine, in the presence of the protease in the blood, a typical emission blue-shift of between about 5 and about 200 nm will be observed. This preferably indicates the presence of a cancerous or precancerous cell in the mammal.

These assay results (from urine or blood) can then be correlated with a prognosis for cancer progression, based upon the specific protease activity detected, as discussed above with regard to the preferred proteases, uPA, MMP-1, MMP-2, and MMP-7, or based upon the speed of the assay, as discussed below.

b. In vivo Methods

In an alternative embodiment, detection of protease activity using the assays may be done in vivo in a mammal. The diagnostic assay, or composition comprising the assay, is preferably administered using a pharmaceutically-acceptable carrier. The assay can be administered by injection into the bloodstream. Alternatively, the assay can be administered by injection to a localized region, such as directly into or near the tumor site.

Delivery to the tumor site for in vivo analysis can be achieved by using liposomes (liposomal delivery). A liposome has a phospholipid bilayer and is preferably stabilized by the addition of cholesterol. Depending on the preparation method, liposome sizes range between 100 nm and several micrometers (preferably from about 100 nm to about 5 μm). Methods of preparing liposomes are known in the art. For example, the liposomes are preferably prepared by dissolving the phospholipids and the assay in a non-aqueous solvent such as chloroform ($CHCl_3$) or tetrahydrofuran (THF) in a reaction vessel (e.g., flask). This solvent is then evaporated using a rotovapor or other distillation device, which results in deposition of a film on the wall of the reaction vessel. A sucrose-solution in water (or any other sugar or salt combination) is then added to the vessel, followed by either freeze-thaw cycles or sonication. The resulting slurry is then preferably extruded through nanoporous filters to form mono-walled liposomes which are more preferred delivery agents.

The liposome containing the assay is then preferably injected into the bloodstream. Advantageously, when injected into the bloodstream, liposomes cannot exit the blood vessels, except in the vicinity of tumors, where blood vessels are "leaky" because of the rapid tumor growth. Therefore, the liposomes preferably become enriched in the vicinity of tumors (i.e., passive targeting). This process can be enhanced by chemically attaching tumor-specific antibodies or aptamers to the liposomes (i.e., active targeting) according to known methods. The liposomes are then preferably destabilized while in the interstitium between the cancer cells to release the assay and detect protease activity in this vicinity.

More preferably, thermolabile liposomes are used. Thermolabile liposomes contain a polymer of the N-isopropylacrylamide type (e.g., a poly(NIPAM/ethylene glycol) block-copolymer), which can be anchored in the phospholipid bilayer of the liposomes via chemically attached long-chain-fatty acids or -alcohols. The liposome can then be heated once it reaches the target site by means of photophysical irradiation at 800 nm using at least two intersecting Ti:sapphire lasers. Preferably, the liposome is heated to a temperature to at least about 38° C., and more preferably at least about 45° C. This will cause the thermocollapse of the thermosensitive liposomes.

Photophysical heating (e.g., plasmonic heating, if nanoparticles are involved) will heat the nanoparticles of the assay, which then will dissipate the heat to the liposomes. That is, when metal nanoparticles are placed in an oscillating electric field, the 'free' electrons will respond to the periodic perturbation. Once the driving electric field is turned off, the oscillation of free electrons rapidly decays on a timescale of a few ps, with the acquired energy ultimately given off as heat due to participation by various scattering processes (i.e. electron-electron, electron-phonon, phonon-surface, etc.). Fast relaxation ensures that heat can be generated repeatedly, and large quantities of energy can be deposited into the nanoparticles. When metal nanoparticles are placed in a solvent bath, this method of heating can lead to a heat source, which is not in thermal equilibrium with its surroundings.

As mentioned, in an alternative embodiment for in-vivo imaging, the assay, dissolved in an aqueous buffer (e.g., phosphate buffered saline (PBS)), can be directly injected into the tumor or tumor-region. In the case of brain tumors, this may be the only viable option.

Once the assay is in the vicinity of the cancerous cells, one or two intersecting Ti:sapphire lasers are preferably used to excite the assay. Other suitable excitation sources include Nd:YAG-lasers (first harmonic at 1064 nm), and any kind of dye-laser, powered by the second harmonic of the Nd:YAG-laser at 532 nm. The light emission from the assay will then be analyzed using a camera, microscope, or confocal microscope. The light emitted from the cancerous regions has a different color than the light emitted from the healthy tissue regions due to the higher activity of the target proteases in the cancerous regions. Advantageously, the cancerous tissue is then visibly discernible to an oncologist or surgeon, for example. Preferably, the Ti:sapphire laser is tuned to a wavelength of about 830 nm for the multi-photon excitation so that only the light emission, but not the excitation can be observed. The assay results can then be correlated with a prognosis for cancer progression, based upon the protease activity detected, as discussed in more detail below.

2. Light-Switch-Based Sensors

In another aspect, the assays utilize a nanoparticle linked by the oligopeptide-cleavage sequence to chromophores/luminophores or quantum dots. More than one chromophore/luminophore or quantum dot may be linked to a single central nanoparticle. However, when multiple particles are utilized, they preferably all comprise the same type of particle. Two preferred assemblies comprise at least one porphryin linked to a nanoparticle or at least one quantum dot linked to a nanoparticle. In this method, the surface plasmon of the core/shell nanoparticle is able to quench the excited state emission spectra from linked porphyrin. Likewise, quantum dots are highly luminescent, except when quenched by the presence of a core/shell metal nanoparticle. Viologens (e.g., methylviologen or propyl viologen-sulfonate (PVS)) can also be used as quenchers.

Once the protease cleaves the consensus sequence, the quantum dot or porphyrin is released and lights up, referred to herein as an "enzyme-triggered light switch." Advantageously, the appearance of a new luminescence/fluorescence band allows for much more sensitive detection. The emission wavelengths of quantum dots depend on their size, and assemblies can be constructed using one color (blue, green, yellow, red) of quantum dot assigned to each target enzyme. Up to four different consensus sequences can be linked to a single nanoparticle (one for each of the colors above). In this manner, the activity of up to four enzymes can be observed in vivo or in vitro at the same time. Preferably, excitation is performed at a wavelength of from about 400 nm to about 500 nm (monophotonic) or from about 800 nm to about 900 nm (multi-photonic). Excitation of the quantum dots can be performed by means of using low intensity visible photon sources, or using ultrafast IR laser pulses. Other suitable excitation sources include Nd:YAG-lasers (first harmonic at 1064 nm), and any kind of dye-laser, powered by the second harmonic of the Nd:YAG-laser at 532 nm. Excitation of porphyrins is preferably performed using tri-photonic excitation with Ti:sapphire laser at 870 nm. The emission from the assay will then be analyzed using a camera, microscope, or confocal microscope. The light-switch-based sensors can be utilized in the exact same procedure (in vitro or in vivo) as the discussed above with regard to the FRET-based sensors.

Using either sensor method (in vitro or in vivo), the assay time of the present invention is dependent upon the concentration of protease present in the sample or tissue. The cleavage speeds will increase by 3-5 times per order of magnitude of increase in protease concentration. In the presence of an aggressive tumor, assay time can be as fast as a fraction of a second. In healthy tissue, it can take about 24 hours for activity to be detected. Thus, the faster the assay, the more aggressive the tumor, and the greater the likelihood of metastatic potential of the tumor. The use of protease-specific oligopeptides for the construction of a nanoparticle-based in vivo nanosensors for the determination of the metastatic potential of solid tumors has never been done before. Preferably, when the assay is directly injected into the tumor region (or suspected tumor region), results can be determined about 30 minutes after injection. When the assay is administered intravenously, the results can be read within about 1 hour after administration of the IV (to permit the assay to reach the target region), and up to 24 hours after administration. In either case, once the assay is in the vicinity of the tumor, protease activity detected within 10 minutes can be correlated with a high probability that the tumor is aggressive. Preferably, if no activity is detected within the first 30 minutes, there is a very low probability that the tumor is aggressive. Likewise, for in vitro testing protease activity detected within 10 minutes can be correlated with a high probability that the tumor is aggressive, whereas no activity within the first 30 minutes after contacting the sample with the assay can be correlated with a very low probability that the tumor is aggressive. This reaction rate provides a distinct advantage over known detection methods which take several hours for assay completion (and results).

EXAMPLES

The following examples set forth preferred methods in accordance with the invention. It is to be understood, however, that these examples are provided by way of illustration and nothing therein should be taken as a limitation upon the overall scope of the invention.

Example 1

Synthesis of Nanoparticle Assembly

In this procedure, the synthesis of a nanoparticle assembly is described. The nanoparticles can be synthesized according to known methods. They are also commercially-available from various sources, for example from Nanoscale Corp. (Manhattan, Kans.) and Sigma Aldrich (St. Louis, Mo.). Suitable nanoparticles for use in the following method include freshly-prepared, non-stabilized nanoparticles, or stabilized nanoparticles. Non-stabilized nanoparticles can be stabilized using ligand exchange as described below.

1. Ligand Exchange

A first set of nanoparticles are dissolved in a non-polar or dipolar aprotic solvent and then treated with 2-aminoethanethiol under pressure (1000 psi) at room temperature for 1 hour. Alternatively, water-soluble nanoparticles can be treated with 2-aminoethanethiol in $H_2O$/acetonitrile mixtures under pressure (1000 psi) at room temperature for 1 hour.

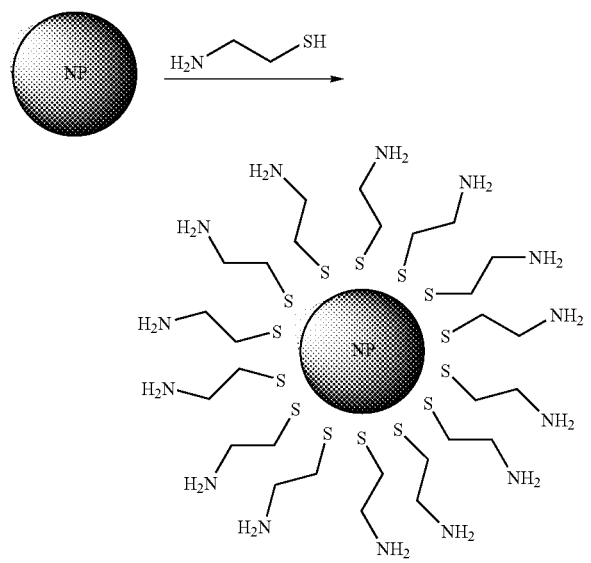

The surface-exchanged nanoparticles are then isolated using preparative Gel Permeation Chromatography (HPLC).

2. Preparation and Attachment of Oligopeptide to Second Nanoparticle

The consensus sequence (cleavage sequence) of the target protease is then selected, and the oligopeptides containing the consensus sequence for coupling the nanoparticles is prepared by using classic peptide synthesis (modified Merrifield synthesis). These oligopeptides are also commercially available from numerous companies such as Genscript (Piscataway, N.J.). The sequence ends with a cysteine on the C-terminal end for reacting with a second set of (non-exchanged) nanoparticles via the thiol group. Its N-terminus is used to react with the first set of surface-exchanged nanoparticles described above. To enhance the binding of the N-terminal end to the second nanoparticle, up to 2 lysine residues can also be added to this end of the oligopeptide. An exemplary oligopeptide structure is illustrated below with one lysine residue attached to the N-terminus of the peptide sequence.

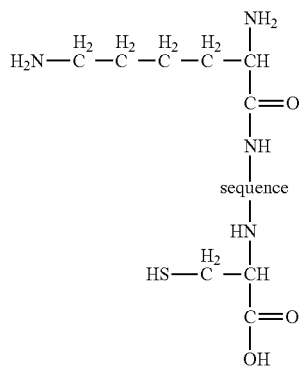

A second set of non-exchanged nanoparticles are then reacted with the oligopeptides in a non-polar, or dipolar aprotic solvent, or aqueous buffer at room temperature under $N_2$ or argon atmosphere for 24 hours. The addition of $NaBH_4$ to the reaction solution ensures that the cysteine units of the oligopeptide do not form disulfide bonds. This reaction has to be performed under dilution conditions (concentration $<10^{-5}$ M) to enable the formation of 1:1 adducts (nanoparticle-oligopeptide) with high yields.

3. Coupling of the First and Second Nanoparticles

To link the two nanoparticles, the surface-exchanged nanoparticle is first treated with carbonyl-bis-imidazol (CDI) in dimethylformamide (DMF) at 40° C. for 1 hour in highly concentrated solution.

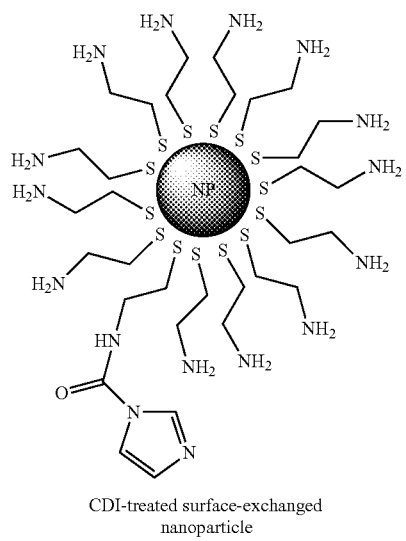

CDI-treated surface-exchanged nanoparticle

The treated surface-exchanged nanoparticle is then added to the non-exchanged nanoparticle-oligopeptide mixture described above. The probability of binding the N-terminal end of the oligopeptide to the surface-exchanged nanoparticle can be enhanced by attaching up to two lysine-residues to the N-terminal end of the oligopeptide linkage.

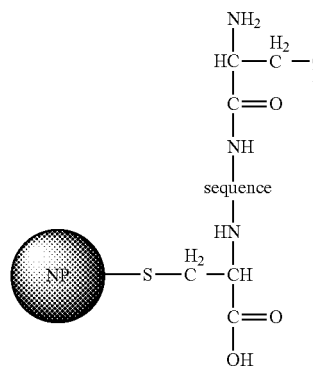
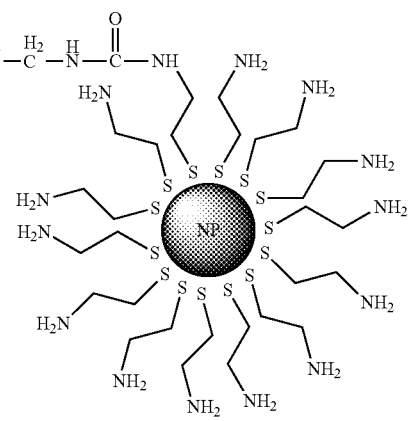

4. Surface-Exchange Treatment of Non-Exchanged Nanoparticle

Finally, the second nanoparticle is treated with 2-aminoethanethiol under high pressure (1000 psi) at room temperature for 1 hour. Alternatively, water-soluble nanoparticles can be treated with 2-aminoethanethiol in H₂O/acetonitrile mixtures under pressure (1000 psi) at room temperature for 1 hour.

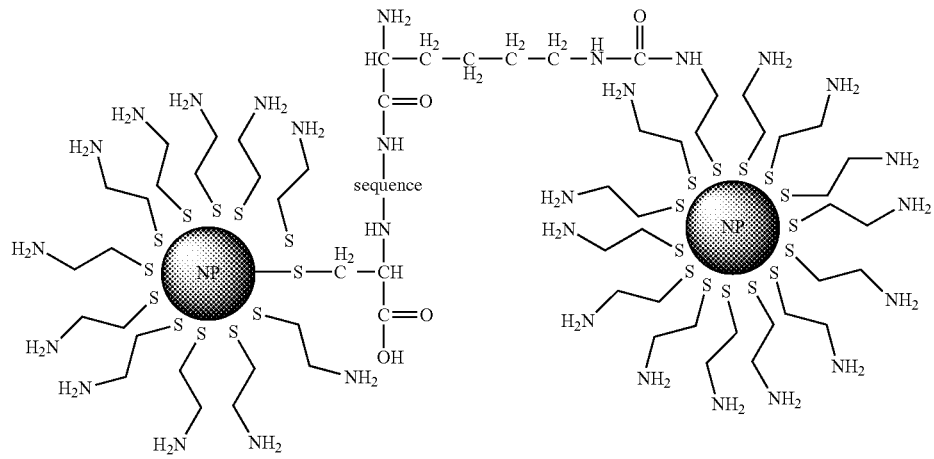

A fraction of the amino groups bind a proton and are negatively charged at pH=7 in aqueous environments. This ensures that the nanoparticles repel each other and the maximal distance is kept, to avoid clustering of the nanoparticles during the assay.

The foregoing procedure can be followed to synthesize nanoparticle assemblies using metal nanoparticles (e.g., Au, Ag, Pt, etc.), nanoparticle-alloys (e.g., AuCu, FePt, CoFe, AuFe, etc.), and core/shell nanoparticles.

Example 2

Preparation of Dye Assemblies

In this procedure, the synthesis of dye assemblies is described. The consensus sequence (cleavage sequence) of the target protease is selected. The oligopeptide containing the consensus sequence for coupling the dyes is then prepared by using classic peptide synthesis (modified Merrifield synthesis), resulting in an exemplary oligopeptide as shown in Example 1. Virtually any fluorescent or phosphorescent dye is suitable for linking to the oligopeptide. However fluorescent dyes or phosphorescent metal complexes possessing a high fluorescence or phosphorescence quantum yield are more suitable. There must be an overlap between the excitation spectrum of the first dye and the fluorescence or phosphorescence spectrum of the second dye in the assembly to permit Förster Energy Transfer (see below). Examples of suitable dyes include all coumarins (especially suited to one- and multi-photon excitation), porphyrins and related compounds, fluoresceine and related compounds, ruthenium polypyridyl complexes, as well as other fluorophores and metal complexes described herein.

The fluorophore or phosphorescent metal complex is linked via an amino-group to a spacer featuring one carboxyl group and one thiol group. The carboxyl group is then used to make a stable amide-bond with the dye. The thiol group is used to link the dye to the C-terminal cysteine group of the oligopeptide. First, the dye is reacted with the spacer using dicyclohexyl-carbodiimide (DCC) with N-hydroxysuccinimide (NHS) as shown below.

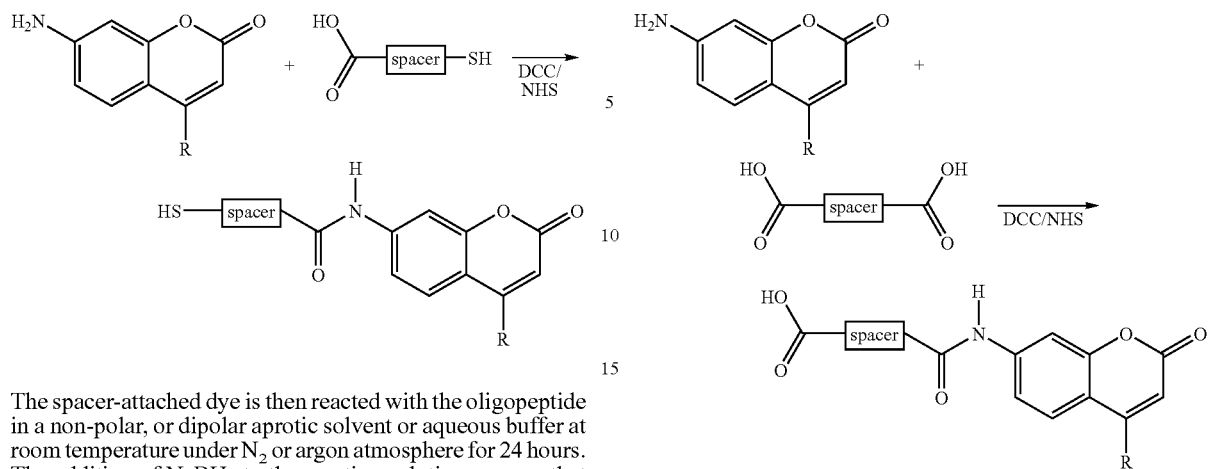

The spacer-attached dye is then reacted with the oligopeptide in a non-polar, or dipolar aprotic solvent or aqueous buffer at room temperature under $N_2$ or argon atmosphere for 24 hours. The addition of $NaBH_4$ to the reaction solution ensures that the cysteine units do not form disulfide bonds. This reaction has to be performed under dilution conditions (concentration $<10^{-5}$ M) to enable the formation of 1:1 adducts (dye-oligopeptide) with high yields.

Alternatively, the dye can be linked to the N-terminal end of the oligopeptide. In this case, the spacer features two carboxyl groups as shown below.

The separation of the final product is performed using reverse-phase (C18) chromatography.

Other fluorophores and metal complexes are linked according to the same methodology, as shown in the examples below.

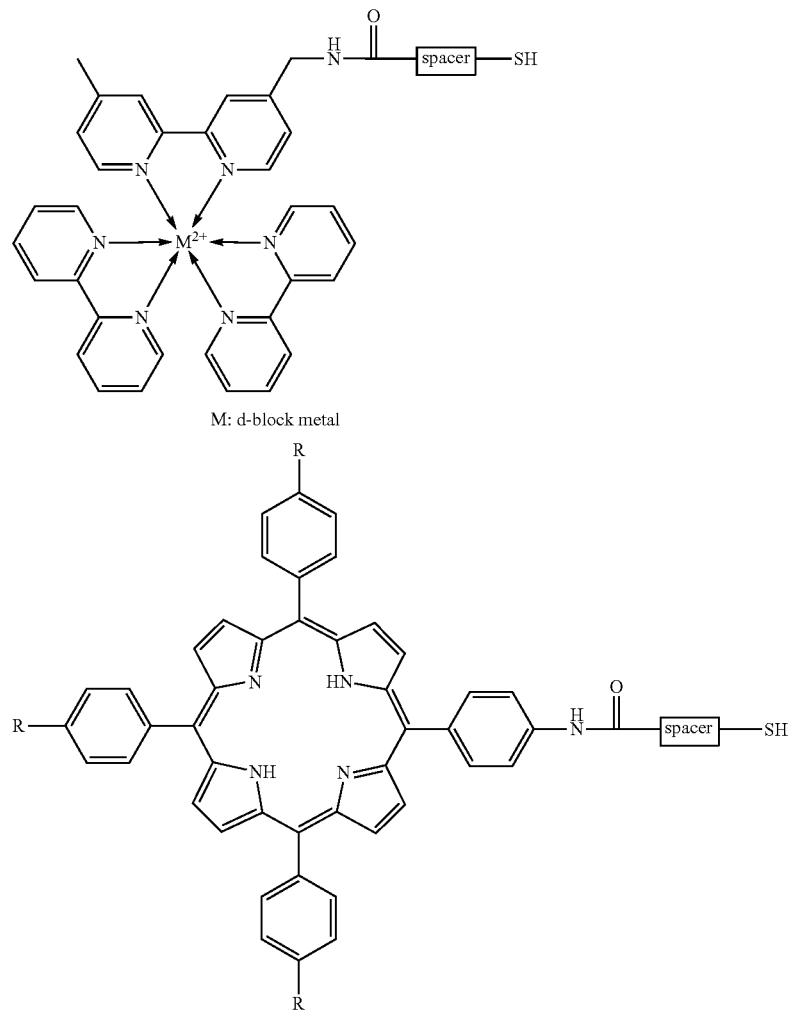

where R=—COOH or N(R$^1$)$_3$, where each R$^1$ is selected from the group consisting of —H, alkyls, and aryls.

Example 3

Nanoparticle-Nanoparticle: Absorption Spectroscopy

In this procedure, UV/Vis-Absorption spectroscopy was used to measure the activity of uPA. All chemicals and solvents were purchased from Fisher/Acros (Pittsburgh, Pa.), unless otherwise noted. A nanoparticle-nanoparticle assembly was prepared using citrate-stabilized gold nanoparticles (Sigma-Aldrich, St. Louis, Mo.) with a 10 nm diameter and an oligopeptide with the following sequence: CGGGSGR-SAGGGC (SEQ ID NO: 35) (GenScript, Piscataway, N.J.). First, 1 mg of the nanoparticles was suspended in 25 ml of tetrahydrofuran (THF) containing $1.0 \times 10^{-3}$ M of glycine. The microheterogeneous solution was heated under pressure (100 psi) and argon-atmosphere to 200° C. for 5 hours. The reaction was carried out using a High-Pressure Reactor (available from Parr Instruments, Moline, Ill.). Digestive ripening decreased the Au-nanoparticle diameter to 4-5 nm. The nanoparticles were then removed from the solution by ultracentrifugation at 30,000 rpm and then resuspended in THF. The procedure was repeated 10 times to remove all non-bonded glycine.

Next, 0.1 mg of the oligopeptide was added to the Au-nanoparticles in 1.0 ml of anhydrous THF, followed by stirring for 24 hours. The oligopeptide and nanoparticles were precipitated by centrifugation at 30,000 rpm and then resuspended in THF. This procedure was repeated 10 times. The linked Au—Au nanoparticle assemblies were then dissolved in phosphate buffer (PBS; pH=7.02), precipitated by centrifugation at 20,000 rpm and resuspended again in PBS.

The reported absorption coefficient at the maximum absorption of the plasmon is $\epsilon = 7.66 \times 10^9$ M$^{-1}$ cm$^{-1}$. This absorption coefficient was used to estimate the concentration of the Au—Au nanoparticles at $1 \times 10^{-4}$ mol.

The Au—Au nanoparticles in PBS solution were then added to a quartz cuvette (~3.0 mL). The solution was heated to 37° C. for 15 minutes. Next, $1 \times 10^{-8}$ mol of urokinase in 0.050 ml of PBS (Innovative Research, Inc., Novi, Mich.) was added to the cuvette.

Figure 2:
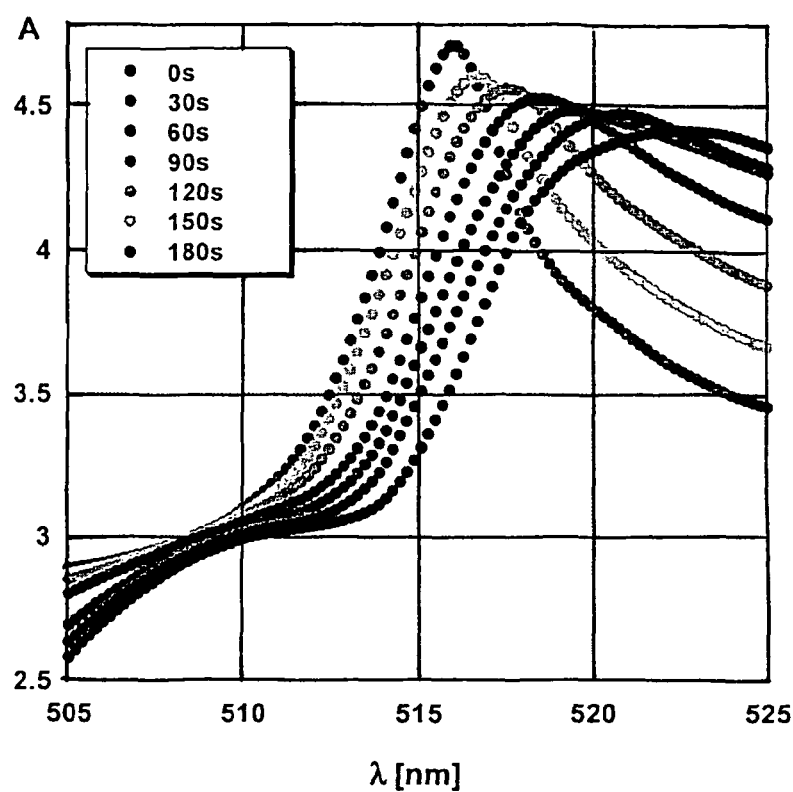
FIG. 2 illustrates the spectral shift in the plasmon absorption of the coupled pair of gold nanoparticles before, during, and after urokinase cleavage of the oligopeptide in Example 3.

The spectral shift in the plasmon absorption of the coupled pair of gold nanoparticles before, during, and after urokinase cleavage of the oligopeptide is shown in FIG. 2. An Agilent 8453 UV-Visible spectrophotometer, equipped with a temperature bath was used to measure the changes in the emission spectrum. The maximum of the gold plasmon absorption was observed to shift from 523 nm to 517 nm within 180 seconds. It is also apparent that the intensity of the plasmon absorption greatly varies at 515 nm (increase) and 525 nm (decrease). The quotient of both measurements will be able to provide reliable time-resolved measurements of the urokinase activity. Urokinase can serve as a model for all proteases shown in Table I.

Example 4

Fluorescence/Phosphorescence Assays

Chromophore-Chromophore Assemblies

In this example, fluorescence/phosphorescence assays were used to measure activity of uPA. A chromophore-chromophore assembly was prepared using the peptide sequence SRSRSRSRSRSGRSAGGGC (SEQ ID NO: 18) (GenScript) as a spacer between a pyrene fluorophore and a coumarin acceptor. All chemicals and solvents were purchased from Fisher/Acros (Pittsburgh, Pa.), unless otherwise noted. The assembly was prepared by dissolving 0.00010 mol of coumarin in THF at room temperature. Next, 0.00012 mol of 1-ethyl-3-(3-dimethyllaminopropyl)carbodiimide (EDC) were added as solid under argon-atmosphere and allowed to react for 5 hours. Then, the oligopeptide linkage was attached to the coumarin by adding to the reaction 0.00010 mol of the oligopeptide dissolved in 1 ml bidest. (double purified) water, followed by stirring at room temperature for 24 hours under argon atmosphere. Next, 0.0020 mol of mercaptopyrene was added as a solid to the solution, and completely dissolved within 5 minutes. The solution was continuously stirred under ambient conditions for another 24 hours.

The solvent was then removed in vacuum and the assembly was purified by HPLC using a reverse phase (C18) column with acetonitrile and PBS as eluent. The resulting chromophore-chromophore assembly is shown below.

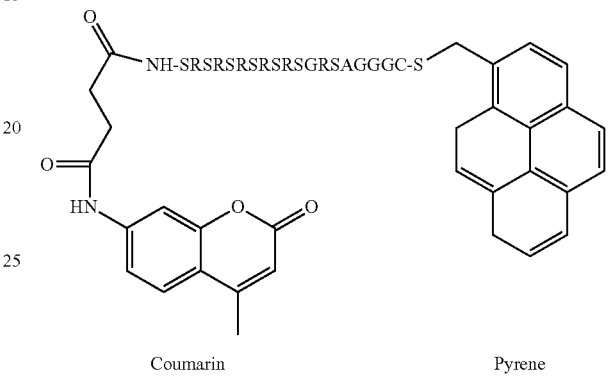

Coumarin    Pyrene

The nanoplatform assembly ($1 \times 10^{-6}$ mol) in PBS was added to a quartz cuvette (~3 mL). The solution was heated to 37° C. for 15 minutes. Then about $1 \times 10^{-8}$ mol urokinase in 0.050 ml PBS (Innovative Research) was added to the cuvette.

Figure 3:
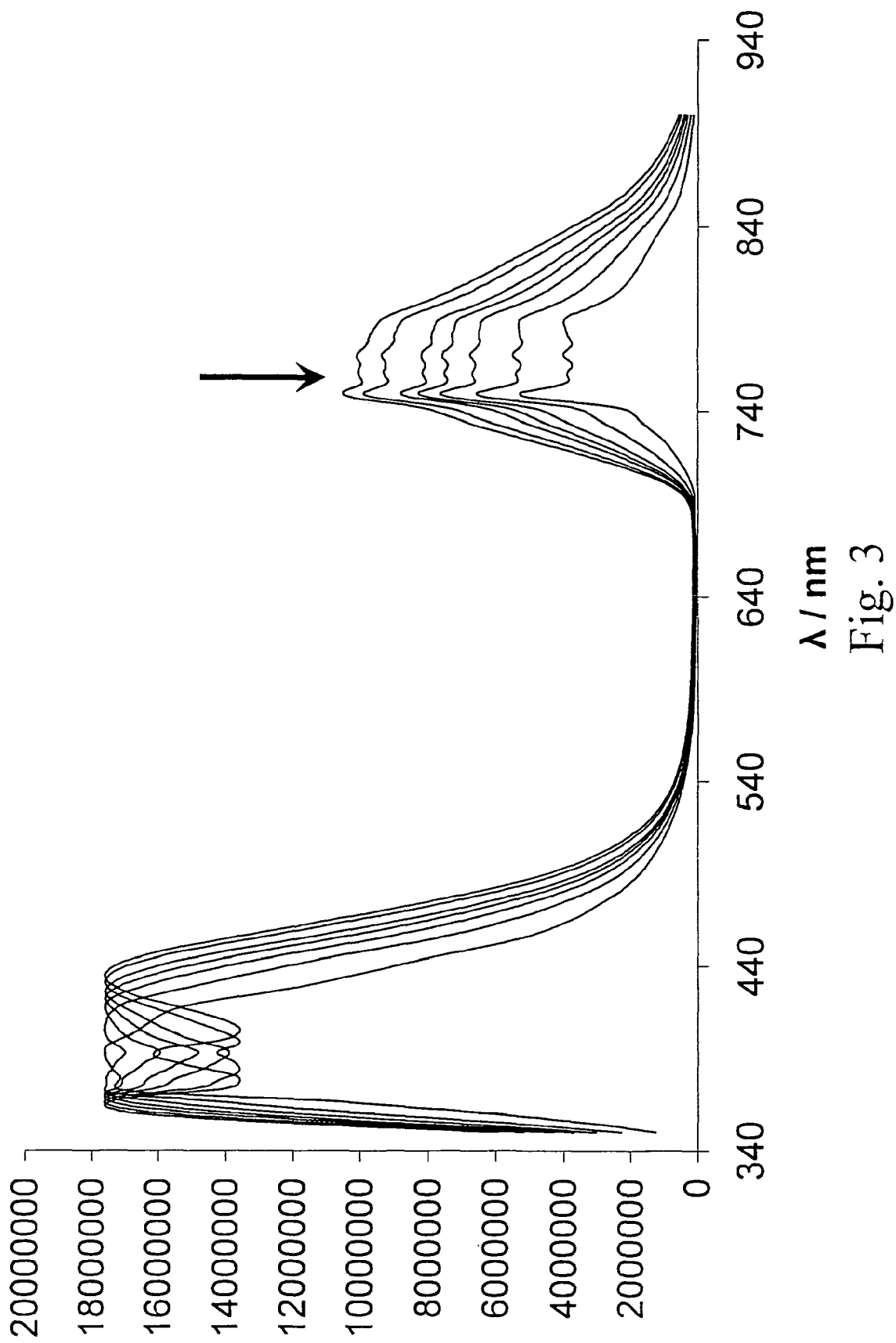
FIG. 3 illustrates the emission spectra of the nanoplatform assembly in Example 4.

The spectral shift from the assay is depicted in FIG. 3. The changes in the emission spectra were measured using a spectrofluorometer (ISA-SPEX, Fluoromax-2; ISA, Inc., Edison, N.J.). Upon photoexcitation of the pyrene at 280 nm, FRET occurs, which causes the attached coumarin to emit most of the phosphorescence/luminescence. The urokinase cleaves the oligopeptide linker between the two chromophores, which drastically changes the observed spectrum. The spectra shows assay time over 0, 2, 4, 6, 8, 10, and 15 minutes. The coumarin emission decreases with time because FRET decreases when the oligopeptide linker is cleaved by urokinase, and the distance between the coumarin and pyrene molecules increases.

Example 5

Stealth-Protection and Optimization of the Porphyrin-Content and -Composition

In this example, stealth ligands featuring chemically-attached metalated and unmetalated tetracarboxy-phenyl-porphyrin (TCPP) were linked to core/shell Fe/Fe$_3$O$_4$-nanoparticles (NanoScale Corporation; Manhattan, Kans.) with oligopeptide linkers. Using porphyrins, two different urokinase-sensors can be created.

1. FRET-Based Sensor

For the FRET-Based Sensor, five Zn-TCPP porphyrins were attached to one central stealth-protected Fe/Fe$_3$O$_4$ nanoparticle, and then a non-metalated TCPP porphyrin was attached to the central nanoparticle, using the procedure described below.

To prepare the stealth-protected Fe/Fe$_3$O$_4$-nanoparticles, 35 mg of dopamine-tetraethylene glycol ligand were dissolved in 5 ml THF. Next, 11.0 mg of Fe/Fe$_3$O$_4$-nanoparticles were added and sonicated at room temperature for 1 hour. The core of the nanoparticles had a diameter of from about 3-5 nm. The $Fe_3O_4$ shell had a thickness of less than 2 nm. The solid was then collected with a magnet and solvent was decanted carefully. The solid was washed with THF (3×3 ml). After drying under vacuum for 2 hours, 10.0 mg of stealth-protected nanoparticle product was obtained.

The oligopeptide linker was then attached to the metalated porphyrin. First, 5.0 mg of the porphyrin was refluxed in 5.0 ml $SOCl_2$ at 100° C. for 30 minutes. The excess $SOCl_2$ was then removed under high vacuum, and the resulting solid was further dried under vacuum for 3 hours. Next, 4 mg of the oligopeptide sequence CGGGSGRSAGGGC (SEQ ID NO: 35) and 5 ml THF were added to the porphyrin solid and stirred at room temperature for 5 hours. The THF was then removed under vacuum, and a greenish-colored solid was obtained. Electrospray ionization (ESI) mass spectrometry showed a mixture of at least 2 linked porphyrin species (mono-peptide and di-peptide linked to porphyrin). The procedure was repeated to attach the oligopeptide linker to the non-metalated porphyrin.

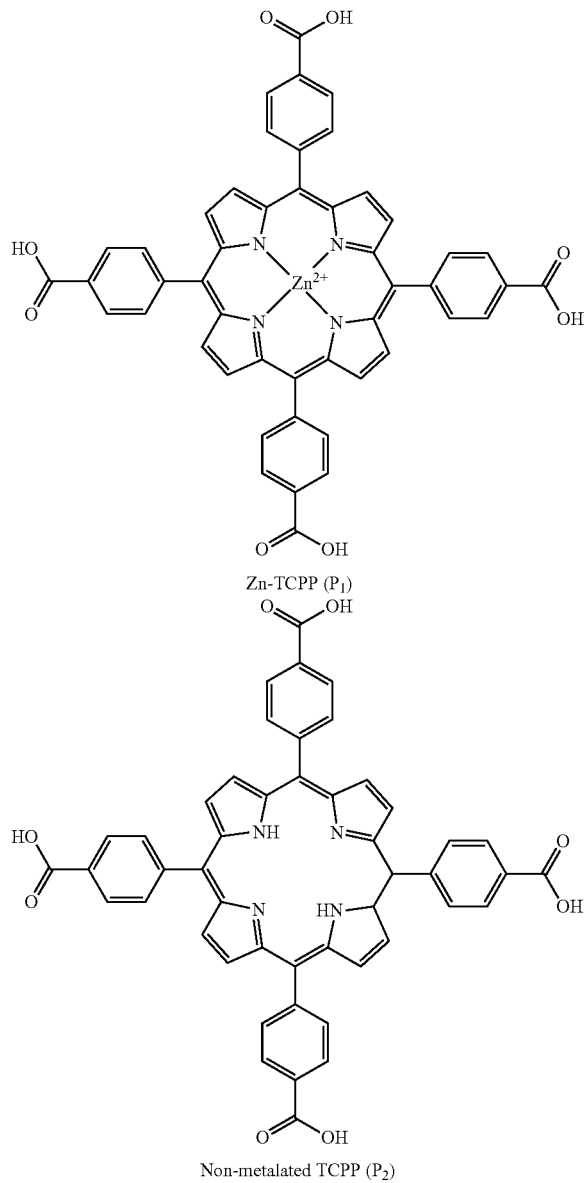

Zn-TCPP ($P_1$)

Non-metalated TCPP ($P_2$)

To attach the porphyrins to the nanoparticles, the metalated porphyrin-oligopeptide solid was dissolved in 10 ml dry THF. Next, 5.0 ml of this solution was added to 10.0 mg of the dopamine tetraethylene glycol-tethered $Fe/Fe_3O_4$ nanoparticles, followed by 1.0 mg 4-dimethylaminopyridine (DMAP) and 8.0 mg EDC. The resulting suspension was sonicated for 1 hour at room temperature. The solid precipitate was collected by magnet and thoroughly washed with THF (8×2 ml). The sample was then dried under high vacuum for 5 hours. 8.0 mg of product was obtained. The procedure was repeated to attach the non-metalated porphyrin to the nanoparticle.

Figure 4:
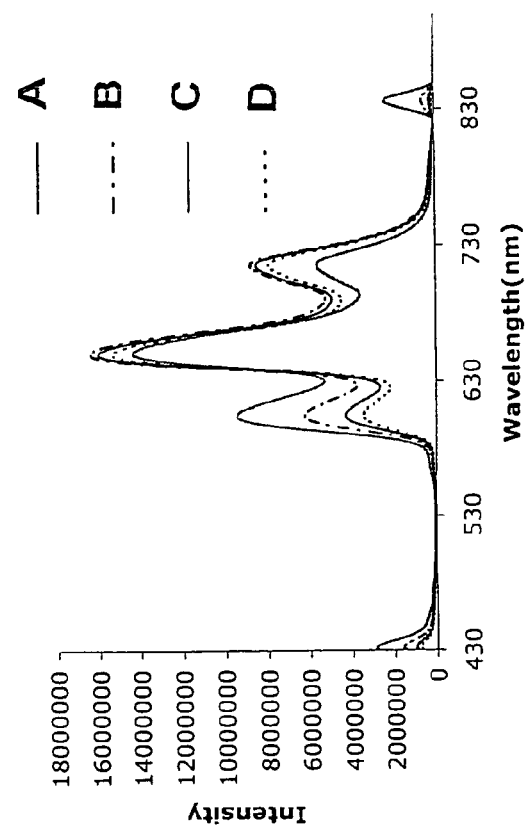
FIG. 4 illustrates the emission spectra of the nanoplatform assembly and FRET-based sensor from Example 5.

The emission spectra of the nanoplatform assembly ($1\times10^{-5}$ M) in PBS in the presence of about $1\times10^{-8}$ M urokinase is depicted in FIG. 4, at 0 (A), 2 (B), 4 (C), and 6 minutes (D). The release of the oligopeptide-tethered TCPP from the $Fe/Fe_3O_4$-nanoparticle by urokinase is visible from the distinct decrease of the fluorescence band at $\lambda_1$=607 nm. The concentration dependence of the fluorescence occurring from the other two fluorescence bands (at $\lambda_2$=654 nm, $\lambda_3$=718 nm) was observed to be non-linear. The reason for the observed non-linear behavior can be found in the high fluorescence quantum yield of the untethered, non-metalated TCPP. We estimated $\Phi$=0.082, which is approximately eight times higher than in the tethered state, when the large porphyrin-concentration in the sphere around the $Fe/Fe_3O_4$-nanoparticle leads to increase FRET and, consequently, radiation-less deactivation of the excited states.

Figure 5:
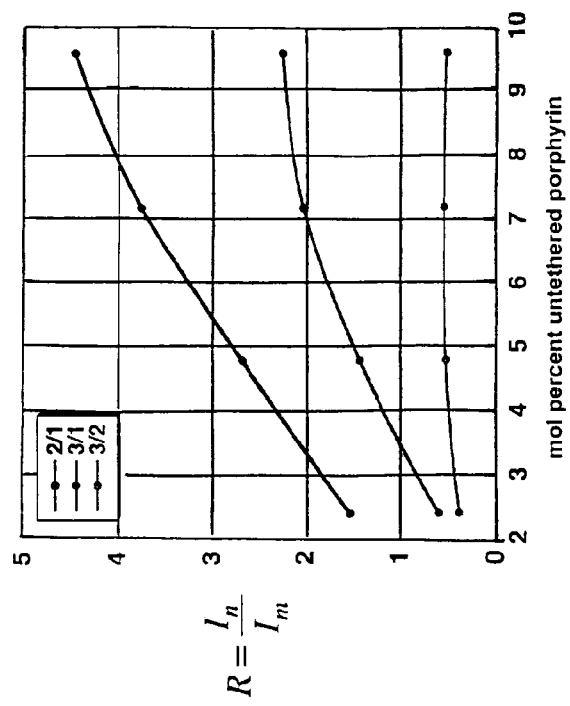
FIG. 5 depicts the ratios of the integrals of the fluorescence bands shown at $\lambda_1=607$ nm, $\lambda_2=654$ nm, and $\lambda_3=718$ nm plotted versus the mol percent of released TCPP in Example 5.

In FIG. 5, the ratios of the integrals of the fluorescence bands shown at $\lambda_1$=607 nm, $\lambda_2$=654 nm, and $\lambda_3$=718 nm are plotted versus the mol percent of released TCPP (as measured by HPLC using an Agilent workstation (HP 1050) equipped with an optical detection system). The plots of $R=I(l_2)/I(l_1)$ and $R=I(l_3)/I(l_1)$ increase with increasing mol percent of released TCPP. The plots are quite linear in the concentration range from 0 to 7 mol percent released TCPP. Therefore, the concentration of TCPP that is released by urokinase, can be measured by recording fluorescence spectra of the nanoplatform at different time intervals and comparing the fluorescence intensities at the three wavelengths ($\lambda_1$, $\lambda_2$, $\lambda_3$). It should be noted that all three wavelengths permit in vivo-measurements in mammalian tissue, especially when coupled with single-photon counting techniques (e.g., fluorescence microscopy).

In this example, tetracarboxy-phenyl-porphyrin (TCPP) was used, but virtually any organic chromophore, metalated chromophore, or quantum dot (e.g., ZnS-stabilized CdSe) can be employed and attached to the nanoparticle via the oligopeptide linker.

Another oligopeptide sequence that was tested using this assembly is KGGSGRSAGGD (SEQ ID NO: 41).

2. "Light-Switch" for Detecting Protease Activity

This type of urokinase sensor is based on the quenching of the excited states of chromophores (e.g. porphyrins) with organic (e.g. viologens) or inorganic quenchers (e.g. metal, alloy, and core/shell nanoparticles). Due to the proximity of the nanoparticles (~2 nm) to the chromophore, the surface plasmon of the core/shell nanoparticle is able to quench the emission spectra from the chemically-attached porphyrin. Once released by urokinase cleavage, the fluorescence or phosphorescence of the chromophore increases significantly. This fluorescence increase can be detected spectrally. When several chromophores featuring discernible emission spectra are used, the activity of various enzymes can be detected simultaneously. The assembly is prepared using the same procedures described above for the FRET-based sensor, except that only one type of porphyrin was used (i.e., non-metalated only or metalated only). This mechanism is depicted below using a bimagentic-nanoparticle linked to a dopamine-tetraethylene glycol ligand featuring a chemically-linked non-metalated TCCP porphyrin with the oligopeptide sequence DGGSGRSAGGK (SEQ ID NO: 36).

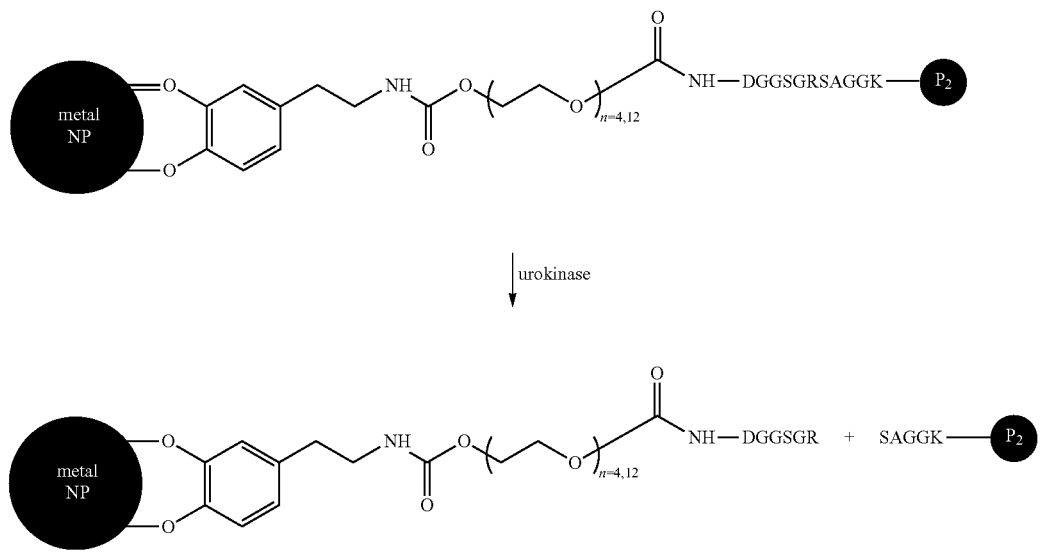

The light-switch mechanism was tested using 3 samples of urine from rats impregnated with MATB III type cancer cells (rodent model for aggressive breast cancer), since urokinase can pass the mammalian kidneys and retains at least some activity in urine. The samples were collected 36, 15, and 5 days after cancer impregnation, respectively, and immediately frozen at −80° C. The tests on the day 36 sample were run twice. Before testing, the urine samples were thawed and allowed to come to room temperature. The following procedure was used to test each sample.

The TCPP-nanoparticle nanoplatform assembly was dissolved in bidest. water using sonication for 30 minutes. Next, 100 μl of urine was added 2.0 ml of the water solution containing 0.1 mg of the nanoplatform. The temperature was kept constant at 34° C. The fluorescence spectra was recorded every 2 minutes for the 36 day and 5 day samples, and ever 1 minute for the 15 day sample.

Figure 6:
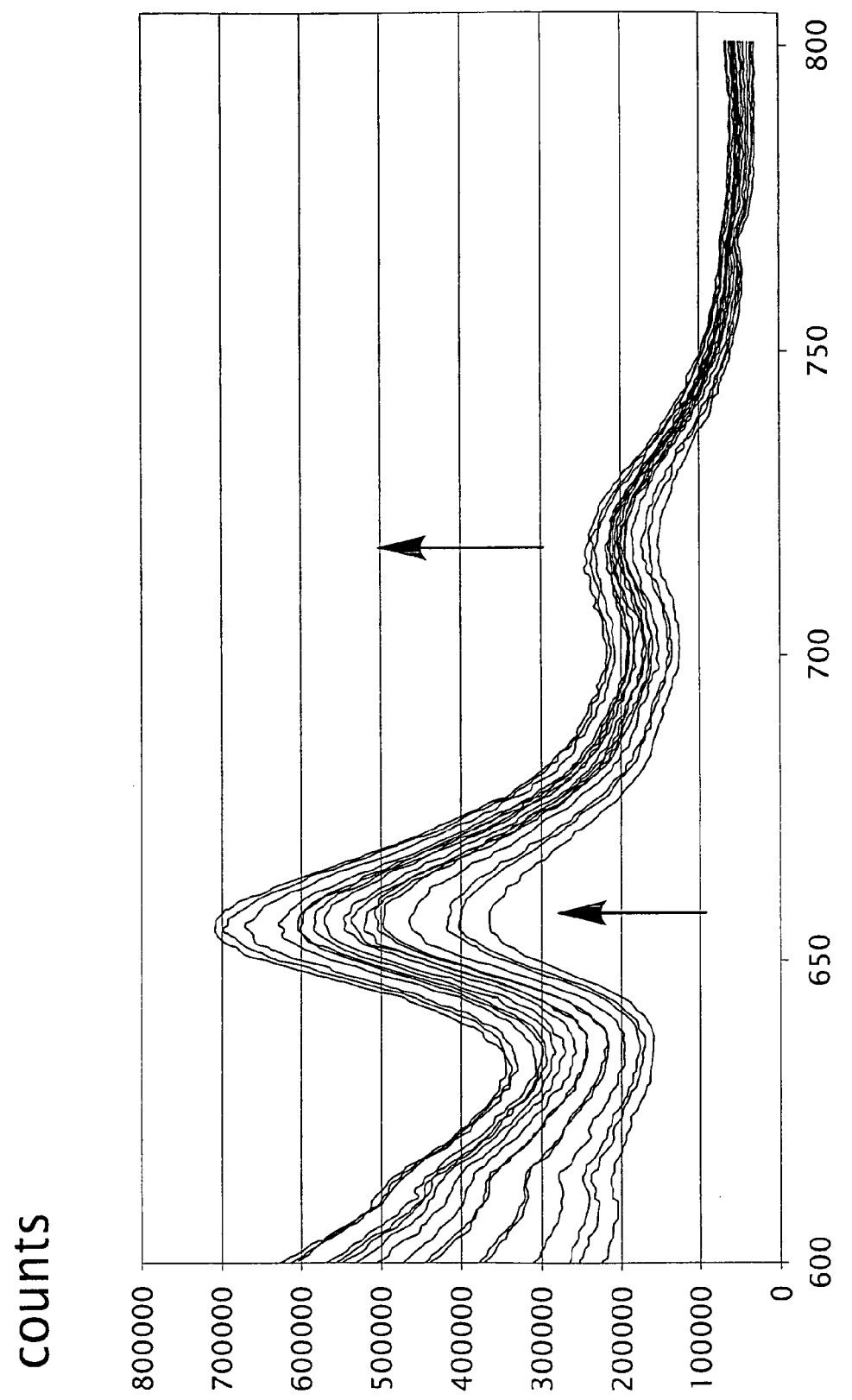
FIG. 6 illustrates the data from the assay in urine from rats impregnated with MATB III type cancer cells using the light switch-based sensor in Example 5.
Figure 7:
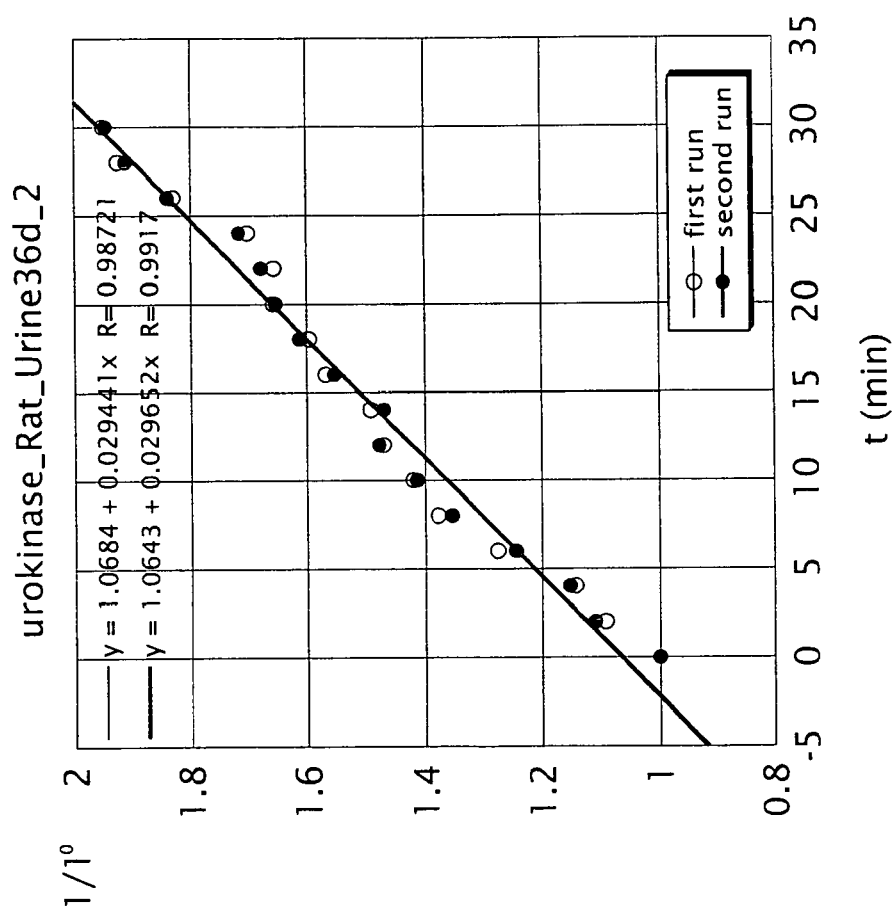
FIG. 7 shows the plot of the relative intensities of the luminescence of TCPP occurring at $\lambda=656$ nm using the data from FIG. 6.

As can be seen from FIG. 6, the luminescence from TCPP increased steadily over time for the 36 day urine. FIG. 7 shows the plot of the relative intensities of the luminescence of TCPP occurring at λ=656 nm using the measurement shown in FIG. 6.

Figure 8:
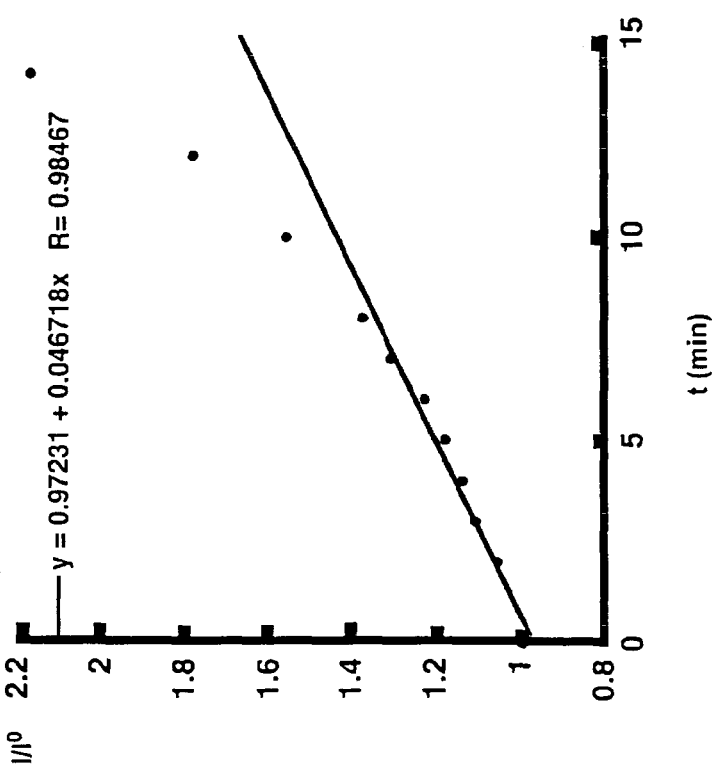
FIG. 8 shows the plot of the relative intensities of the luminescence of TCPP occurring at $\lambda=656$ nm when measuring urine of rats, which have been impregnated with MATBIII cells 15 days prior to sampling the urine in Example 5.

FIG. 8 shows the plot of the relative intensities of the luminescence of TCPP occurring at λ=656 nm from the 15 day sample.

Figure 9:
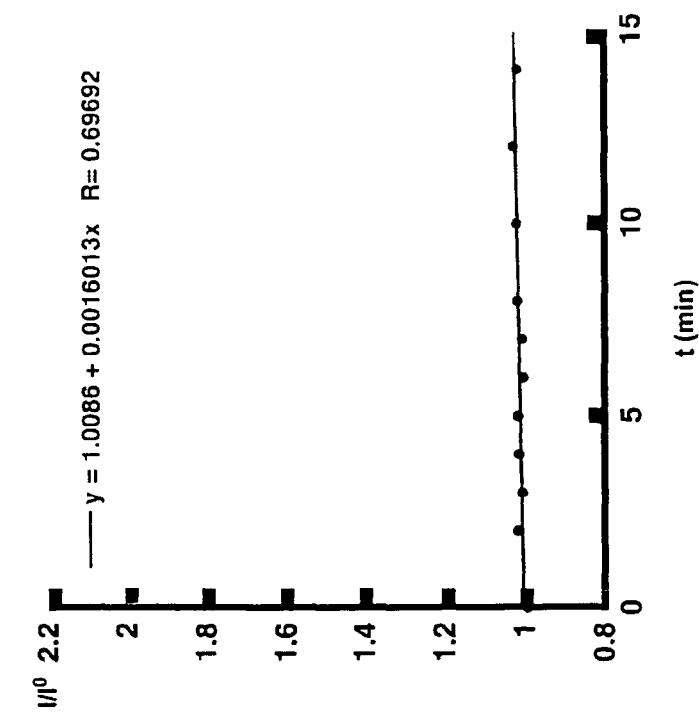
FIG. 9 shows the plot of the relative intensities of the luminescence of TCPP occurring at $\lambda=656$ nm when measuring urine of rats, which have been impregnated with MATBIII cells 5 days prior to sampling the urine in Example 5.

The rat urine which was collected only 5 days after impregnation of the rats with MATB III tumor cells, does not show any discernible urokinase activity, as shown in FIG. 9. The urine data correlates nicely with the observed growth curves of MATB III tumors in rats, where the maximum of tumor growth can be discerned approximately 2 weeks after the impregnation of the MATB III cells. However, after stem cell therapy, the tumors are significantly attenuated by day 36.

Example 6

Quantum Dot Assemblies

In this example, the preparation of nanoplatform assemblies of CdSe/ZnS core/shell quantum dots linked to gold coated $Fe_2O_3$ nanoparticles is described. The CdSe/ZnS quantum dots will be in their 'OFF' state when initially attached to the gold surface of the nanoparticle, due to the quenching effects of the nanoparticle. Once the oligopeptide is cleaved by the enzyme urokinase, the CdSe/ZnS is released and becomes fluorescent. This enzyme-triggered light switch indicates the presence of the target enzyme. An Au/Fe alloy nanoparticle can also be used instead of the $Fe_2O_3$ nanoparticles.

1. Synthesis of Quantum Dots

Figure 10:
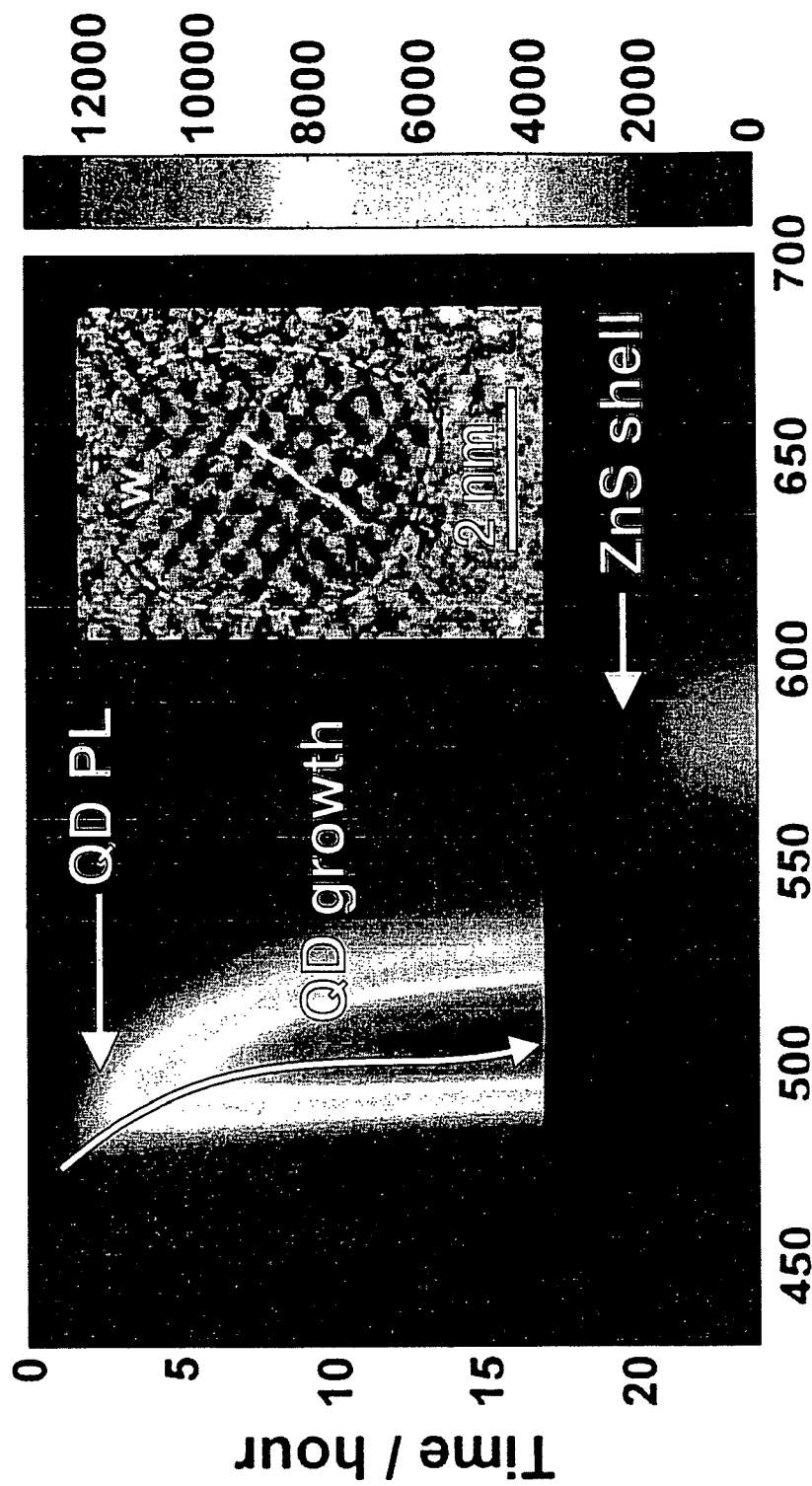
FIG. 10 illustrates the growth of CdSe quantum dots during synthesis as indicated by their luminescence from Example 6. The inset shows a representative image of a highly crystalline CdSe quantum dot with wurzit structure.

Synthesis of CdSe/ZnS quantum dots is well established. The synthesis takes place at 120° C. in hexadecyl amine using a single precursor $Li_4[Cd_{10}Se_4(SPh)_{16}]$ to form the CdSe core. The precursor slowly decomposes over many hours resulting in high quality crystals. Once the synthesis is complete, the ZnS shell is grown over the CdSe core as indicated by an in situ photoluminescence technique at high temperature, allowing very sensitive control over the reaction conditions. The growth of the quantum dots is shown by the shift of the photoluminescence (PL) emission maximum, as depicted in FIG. 10. When the quantum dots are heated to 250° C., the emission of the uncoated quantum dots is strongly quenched. At the overcoating step, the emission of the quantum dots reappears, even at 250° C.

Quantum dots have very large photoluminescence yields along with very large absorption cross-sections, which decreases the thermal load on the biological system. If different color emission is needed for creating multiple sensors (multiplex detection) this can be achieved by changing the size of the quantum dot core yielding different emission wavelengths. CdSe can be easily tuned between 500-650 nm with size change. While these quantum dots can be grown to virtually any size, the growth of the quantum dots will be restricted to less than 5.5 nm so that the nanoplatform can efficiently leave the filtration system of the body (renal pathway) when used in vivo.

2. Stabilization of Quantum Dots

Although CdSe/ZnS quantum dots are sufficiently stable towards bio-corrosion, the binding of an amphiphilic resorcinarene-ligand will greatly enhance their water-solubility and enable the binding of the oligopeptide sequence containing the protease consensus sequence, especially when the following sequences are utilized: a) KGGGSGRSAGGGC for urokinase; b) KGGVPMS-MRGGGC, for MMP1; c) KGGIPVS-LRSGGC for MMP2; and d) KGGVPLS-LT-MGGC for MMP7, where "-" indicates the point of protease cleavage. The ligand creates a monolayer shell around the quantum dot. A preferred resorcinarene ligand for quantum dot stabilization (as well as nanoparticle stabilization) is illustrated below.

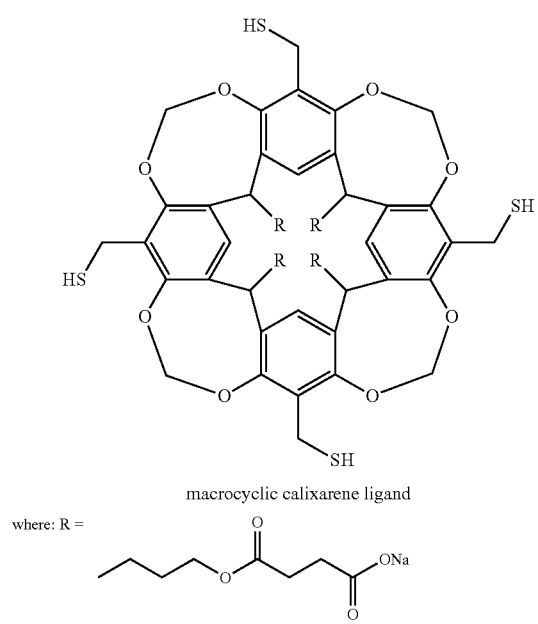

macrocyclic calixarene ligand where: R = [structure showing chain with O, C=O, O, C=O, ONa groups]

The monolayer can be formed on the quantum dot surface in either a non-aqueous liquid (e.g., THF, DMF, acetonitrile) or in an aqueous buffer (e.g., PBS, water/THF-mixtures, or water-alcohol-mixtures), depending on the selected synthesis route of the quantum dot (or nanoparticle). A nanoparticle or quantum dot of 5 nm in diameter requires 55 resorcinarene ligands for the formation of a monolayer. The ligand is amphiphilic (log P=4.7).

3. Attachment of Oligopeptides to Stabilized Quantum Dot

The next step in the assembly of the nanoplatform will be the chemical attachment of the oligopeptide linkers to the pendant carboxylic acid groups at the "feet" of the resorcinarene-ligands, which are stabilizing the CdSe/ZnS quantum dots. The oligopeptides are commercially available. Binding of the terminal lysine residue of the oligopeptide to the resorcinarene-carboxylates will be achieved by using the well-known DCC/NHS/HOBT-method, which is a standard procedure in protein synthesis and bioconjugation. Each cleavage sequence will be bound to one particular quantum dot featuring a distinct luminescence maximum (blue, green, yellow, or red depending upon size), allowing for multiplex detection of enzyme activity. The separation of the quantum dots from the reaction solvent will be achieved by centrifugation. After linking, the quantum dot is then transferred stepwise into an aqueous buffer (PBS) again.

Electrospray/time-of-flight mass spectrometry is suitable for determining the total mass of the assemblies, which permits the determination of the surface coverage of the oligopeptides over the surface of the stabilized quantum dot. It is important that the layer of attached oligopeptides featuring the cleavage site is somewhat incomplete (max. of about 75 percent surface coverage) to permit the attack of target protease (e.g., urokinase), which would be impeded by sterical factors if a perfect coverage is achieved (although the DCC/NHS/HOBT method may not be efficient enough to permit such coverage). An extra HPLC-step will be used to obtain highly pure oligopeptide. The oligopeptide coverage over the surface of the quantum dot can be varied systematically, beginning with 25% surface coverage. The EDC/NHSS-method, which is adapted for protein synthesis and bioconjugation in aqueous solvents can also be employed.

4. Attachment of the Quantum Dots to the Gold Coated Iron Oxide Nanoparticle

Next, the CdSe/ZnS quantum dots are linked to the $Fe_2O_3$/Au nanoparticles via the cysteine residue on the C-terminal end of the oligopeptide linkers. To determine the activity of one enzyme, one kind (size) of quantum dot will be linked to the nanoparticle. However, for the in vivo determination of cancer progression, up to four different quantum dots (featuring different oligopeptide sequences) will be bound to a single gold coated nanoparticle. This reaction is carried out by binding the terminal cycseine-residues of the cleavage sequence to the gold shell around the iron oxide nanoparticle. Molecular modeling was used to determine that the length of each of the four oligopeptides will be less than 4.5 nm. Therefore, the total distance between the $Fe_2O_3$/Au nanoparticle and stabilized CdSe/ZnS quantum dot will be approximately 5 nm (i.e., resorcinarene ligand+oligopeptide linker), which is the optimal distance for maximal luminescence quenching of the quantum dots by the Au nanoshell when tethered.

Example 7

Test of an In-Vivo Sensor for Urokinase Using Fluorescence Microscopy

Figure 11:
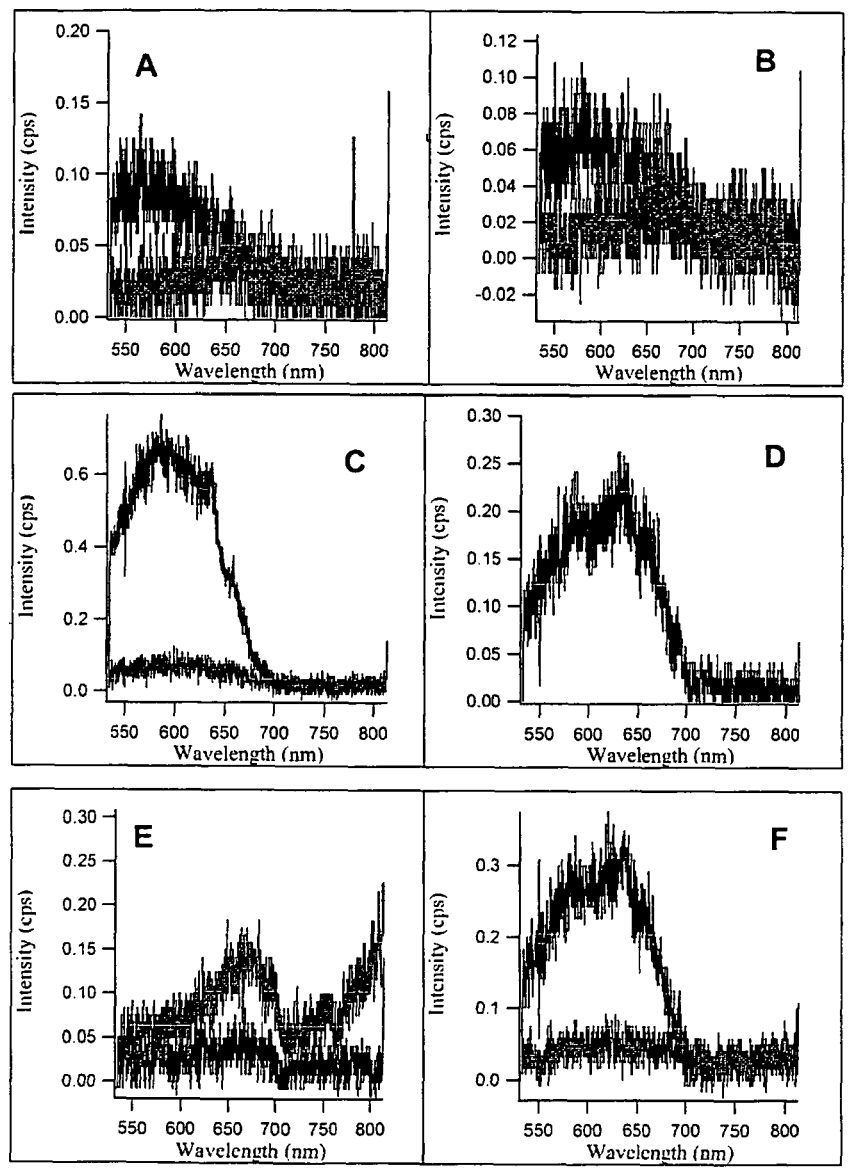
FIG. 11 illustrates the single-photo-counting spectra, from the right and left limbs of the mice from Example 7, recorded through a fluorescence microscope.

The in-vivo urokinase-assay was tested in Charles River female mice, which have been impregnated with B16F19 mouse melanoma cells 10 days prior to these measurements. The mice were anesthetized and then a solution of a Fe/$Fe_3O_4$-nanoparticle-TCPP assembly was administered to the mice intravenously (IV) or via direct injection into the tumors (IT). The IV solution was 200 µg of the nanoparticle assembly in 200 ml PBS. The IT solution was 100 µg of the nanoparticle assembly in 200 ml PBS. To measure the activity of the assay, the mice were anesthetized again and placed under a fluorescence microscope employing a single-photo-counting detector. This instrument has been built in-house. The results of the single-photo-counting spectra, from the right and left limbs of the mice, recorded through a fluorescence microscope (resolution: 1 m×1 m×1 m) is illustrated in FIG. 11 (red: left limb; blue: right limb). Box A shows the results from mouse 1, which was IT-injected 30 minutes prior to measurement. Box B shows the results from mouse 2 (no tumors), which was IV-injected 12 hours prior to measurement. Box C shows the results from mouse 3 (bearing tumors on both legs), which was IV-injected 12 hours prior to measurement. Box D shows the results of mouse 4, which was IV-injected 24 hours prior to measurement. Box E shows the results from the control mouse, neither IT- nor IV-injected. Box F is a repeat of C from mouse 7.

The tumor regions at the hind legs of the mice were excited using laser light (Ti:sapphire-laser, $\lambda$=870 nm, P=6.5 mW) in the IR-region. TCPP requires tri-photonic excitation at this excitation wavelength. It is remarkable that the signal strengths obtained in the right legs of the tumor-bearing mice correlates with the tumor size, whereas the signal in the left limb apparently does not. The hypothesized explanation is that the uptake of the nanoparticle assembly by the tumors is so quick, that the first tumor, which is encountered by the injected intravenously, incorporates almost everything. It was found that the IT-injection is less efficient than IV-injection, because the urokinase does not have the time to cleave the majority of the cleavage sequences and the porphyrin does not light up.

Example 8

Measurements of Urokinase Activity in PBS

In this example, a calibration curve was recorded to demonstrate how urokinase activity (as a model for all proteases discussed herein) changes with increasing urokinase concentration. The changes in the emission spectra were measured using a spectrofluorometer (ISA-SPEX, Fluoromax-2; ISA, Inc., Edison, N.J.). All chemicals and solvents were purchased from Fisher/Acros, unless otherwise noted.

The pH of the urine of a healthy rat is 6.7±0.4. Therefore, the curve was recorded in PBS (pH=6.8) using four concentrations of urokinase: $1\times10^{-10}$ M, $1\times10^{-9}$ M, $5\times10^{-8}$ M (2×) and $1\times10^{-8}$ M. Fe/Fe$_3$O$_4$ nanoparticle-TCPP assemblies featuring the urokinase cleavage sequence were dissolved in PBS. The nanoparticle assembles were first dissolved in water at a concentration of 0.5 mg of nanoparticles per 1 ml of water, followed by sonication for 30 minutes to render the nanoparticles soluble in the water. Next, 2.0 ml of water containing 0.1 mg of the nanoplatform was mixed with the PBS. The temperature was kept constant at 34° C. Continuous excitation was done at 417 nm. Fluorescence spectra were recorded at constant time intervals (10 min, 5 min, 2 min or 1 min, depending on the concentration. The urokinase was then added to the PBS mixture. The emission band at 656 nm was monitored.

Figure 12:
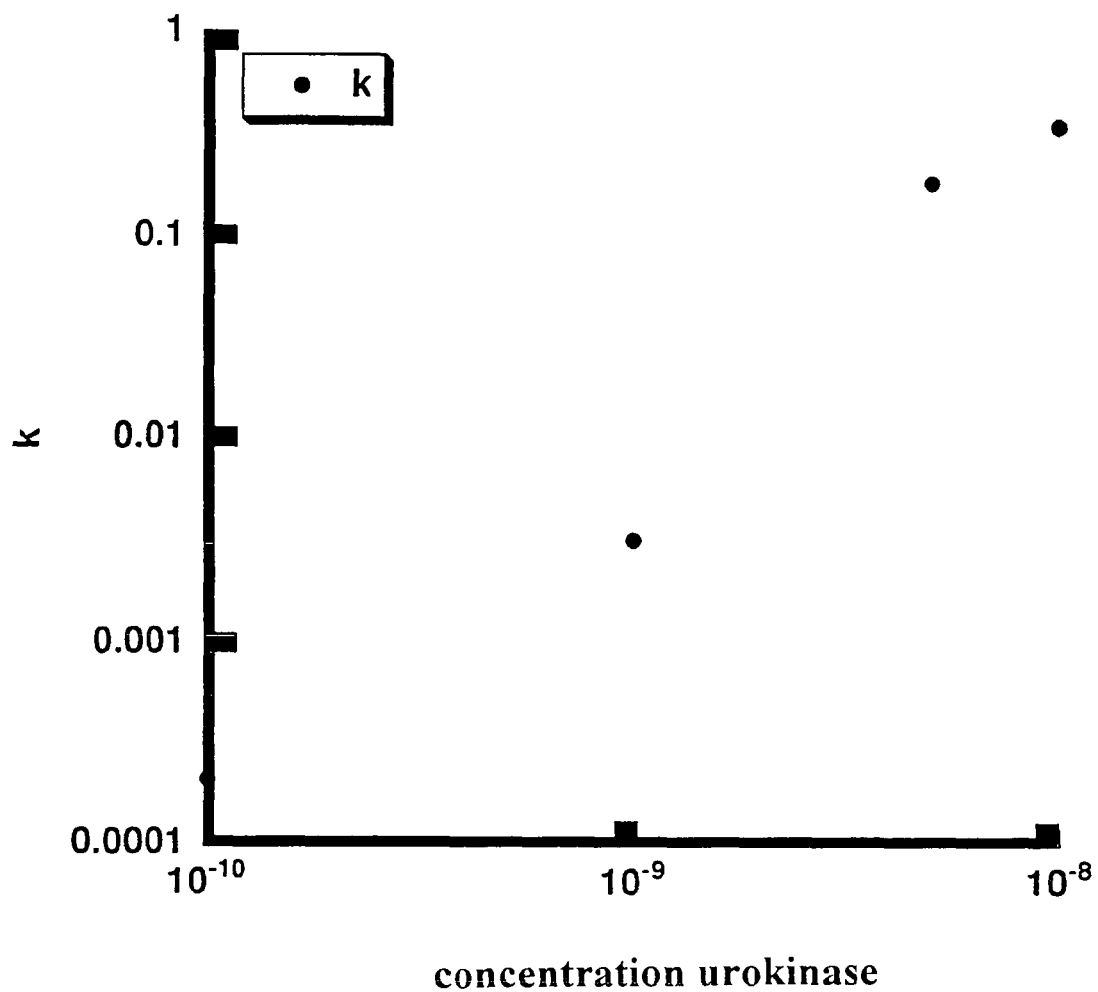
FIG. 12 illustrates the calibration curve results from Example 8.

The results are shown in FIG. 12, where k is the rate constant obtained by plotting (I: luminescence intensity)/(I$_0$: luminescence intensity prior to adding urokinase) vs. time (in seconds). As can be seen from the graph, the cleavage rate increases by 3-5 times per order of magnitude of increase in urokinase concentration. Thus, the speed of cleavage can be correlated with the aggressiveness of the tumor.

We claim:

1. A nanoplatform assembly for detecting protease activity comprising:
   a first particle, wherein said first particle is a core/shell nanoparticle, said core being selected from the group consisting of Au, Ag, Cu, Co, Fe, and Pt, and said shell being selected from the group consisting of Au, Ag, Cu, Co, Fe, Pt, the metal oxides thereof, and combinations thereof;
   a second particle, wherein said second particle is selected from the group consisting of nanoparticles, chromophores/luminophores, quantum dots, viologens, and combinations thereof; and
   a linkage between said first and second particles, wherein said linkage comprises a protease consensus sequence, and wherein said linkage separates said first and second particles by a distance such that said first particle quenches an excited state of said second particle.

2. The assembly of claim 1, wherein said first and second particles each have respective diameters of from about 1 to about 100 nm.

3. The assembly of claim 1, wherein said core/shell nanoparticle is selected from the group consisting of Fe/Au, Fe/Fe$_3$O$_4$, Fe/Fe$_x$O$_y$, and Au/Fe$_2$O$_3$.

4. The assembly of claim 1, wherein said core/shell nanoparticle is a stabilized nanoparticle comprising an organic monolayer surrounding the nanoparticle.

5. The assembly of claim 4, wherein said monolayer is comprised of ligands, said ligands comprising at least one member selected from the group consisting of thiols, alcohols, nitro compounds, phosphines, phosphine oxides, resorcinarenes, selenides, phosphinic acids, phosphonicacids, sulfonic acids, sulfonates, carboxylic acids, disulfides, peroxides, amines, nitriles, isonitriles, thionitiles, oxynitriles, oxysilanes, alkanes, alkenes, alkynes, aromatic compounds, and seleno moieties.

6. The assembly of claim 1, wherein said second particle is a chromophore or luminophore.

7. The assembly of claim 6, wherein said chromophore or luminophore is selected from the group consisting of organic dyes, inorganic dyes, fluorophores, phosphophores, light absorbing nanoparticles, combinations thereof, and the metalated complexes thereof.

8. The assembly of claim 7, wherein said chromophore or luminophore is an organic dye selected from the group consisting of coumarins, pyrene, cyanines, benzenes, N-methyl-carbazole, erythrosin B, N-acetyl-L-tryptophanamide, 2,5-diphenyloxazole, rubrene, and N-(3-sulfopropyl)acridinium, an inorganic dye selected from the group consisting of porphyrins, phthalocyanines, chlorins, and metalated chromophores, or a fluorophore or phosphophor selected from the group consisting of phosphorescent dyes, fluoresceines, rhodamines, and anthracenes.

9. The assembly of claim 8, wherein said chromophore or luminophore is a porphyrin selected from the group consisting of tetra carboxy-phenyl-porphyrin (TCPP) and Zn-TCPP.

10. The assembly of claim 1, wherein said second particle is a quantum dot.

11. The assembly of claim 1, wherein said linkage is comprised of an oligopeptide containing said consensus sequence.

12. The assembly of claim 1, wherein said consensus sequence is selected from the group consisting of a serine protease cleavage sequence, an aspartate protease cleavage sequence, a cysteine protease cleavage, and a metalloprotease cleavage sequence.

13. The assembly of claim 1, wherein said consensus sequence is selected from the group consisting of SGRSA (SEQ ID NO: 2), VPMSMRGG (SEQ ID NO: 3), IPVSLRSG (SEQ ID NO: 4), RPFSMIMG (SEQ ID NO: 5), VPLSLTMG (SEQ ID NO: 6), VPLSLYSG (SEQ ID NO: 7), IPESLRAG (SEQ ID NO: 8), SGSPAFLAKNR (SEQ ID NO: 9), DAFK (SEQ ID NO: 10), SGKPILFFRL (SEQ ID NO: 11), SGKPIIFFRL (SEQ ID NO:12), GPLGMLSQ (SEQ ID NO:13), HGPEGLRVGFYESDVMGRGHARLVHVEEPHT (SEQ ID NO: 25), GPQGLAGQRGIV (SEQ ID NO: 26), SLLKSRMVPNFN (SEQ ID NO: 27), SLLIFRSWANFN (SEQ ID NO: 28), and SGVVIATVIVIT (SEQ ID NO: 29).

14. The assembly of claim 1, wherein said linkage is selected from the group consisting of SRSRSRSRSRSGRSAGGGC (SEQ ID NO: 18), KGGVPMSMRGGGC (SEQ ID NO: 30), KGGIPVSLRSGGC (SEQ ID NO: 31), KGGVPLSLTMGGC (SEQ ID NO: 32), KGGGSGRSAGGGC (SEQ ID NO: 33), CGGGSGRSAGGC (SEQ ID NO: 34), CGGGSGRSAGGGC (SEQ ID NO: 35), DGGSGRSAGGK (SEQ ID NO: 36), and KGGSGRSAGGD (SEQ ID NO: 41).

15. The assembly of claim 1, further comprising up to 9 additional particles, each of said additional particles being linked to said first particle by respective linkages, wherein each of said linkages comprises a protease consensus sequence.

16. A composition comprising a diagnostic assay including the assembly of claim 1 and a pharmaceutically-acceptable carrier.

* * * * *